United States Patent [19] [11] Patent Number: 5,246,853
Clarkson et al. [45] Date of Patent: Sep. 21, 1993

[54] METHOD FOR TREATING COTTON-CONTAINING FABRIC WITH A CELLULASE COMPOSITION CONTAINING ENDOGLUCANASE COMPONENTS AND WHICH COMPOSITION IS FREE OF EXO-CELLOBIOHYDROLASE I

[75] Inventors: Kathleen A. Clarkson, San Francisco; Edward Larenas, San Carlos; Geoffrey L. Weiss, San Francisco, all of Calif.

[73] Assignee: Genencor International, Inc., So. San Francisco, Calif.

[21] Appl. No.: 678,865

[22] Filed: Mar. 29, 1991

Related U.S. Application Data

[63] Continuation-in-part of Ser. No. 593,919, Oct. 5, 1990, abandoned.

[51] Int. Cl.$^5$ .................. D06M 16/00; C12N 9/42; C12N 1/00
[52] U.S. Cl. .................. 435/263; 435/209; 435/945
[58] Field of Search .................. 435/209, 945, 263

[56] References Cited

U.S. PATENT DOCUMENTS

| | | |
|---|---|---|
| 4,435,307 | 3/1984 | Barbesgaard et al. .......... 252/174.12 |
| 4,479,881 | 10/1984 | Tai .................................. 252/8.8 |
| 4,648,979 | 3/1987 | Parslow et al. ................ 252/8.8 |
| 4,738,682 | 4/1988 | Boegh et al. ..................... 8/401 |
| 4,822,516 | 4/1989 | Suzuki et al. ................ 252/174.12 |
| 4,832,864 | 5/1989 | Olson ............................ 252/174.12 |
| 4,894,338 | 1/1990 | Knowles et al. .............. 435/172.3 |
| 4,945,053 | 7/1990 | Ito et al. ......................... 435/209 |

FOREIGN PATENT DOCUMENTS

| | | |
|---|---|---|
| 0120528 | 10/1984 | European Pat. Off. . |
| 0173397 | 3/1986 | European Pat. Off. . |
| 0244234 | 11/1987 | European Pat. Off. . |
| 2148278C2 | 3/1972 | Fed. Rep. of Germany . |
| 58-36217 | 3/1983 | Japan . |
| 58-54082 | 3/1983 | Japan . |
| 64-40681 | 2/1989 | Japan . |
| 89/09259 | 10/1989 | PCT Int'l Appl. . |
| 2094826 | 9/1982 | United Kingdom . |
| 2095275 | 9/1982 | United Kingdom . |

OTHER PUBLICATIONS

Bhat et al., (1989) Carbohydrate Research vol. 190, pp. 279-297.
Brown and Gritzali, (1984) Genetic Control of Environmental Pollutants, Omenn Editor, Plenum Publisher pp. 239-265.
Chen et al., (1987) Biotechnology, vol. 5, pp. 274-278.
Coughlan et al., (1988) Biochemistry and Genetics of Cellulose Degradation, Aubert et al. eds., pp. 11-30.
Hayashida et al., (1988) Methods in Enzymology, vol. 160 pp. 323-332.
Hayashida et al., (1980) Agric. Biol. Chem. vol. 44(8) pp. 1721-1728.
International Textile Bulletin Dyeing/Printing/Finishing (2nd Quarter, 1990) pp. 5 et seq.
JTN "Whats New—Weight Loss Treatment to Soften the Touch of Cotton Fabric" (Dec. 1988).
Kenkyushitsu and Yamagishi, "The Improvement of Cellulose Fibers by Means of Cellulase".

(List continued on next page.)

Primary Examiner—David M. Naff
Assistant Examiner—Michael Meller
Attorney, Agent, or Firm—Burns, Doane, Swecker & Mathis

[57] ABSTRACT

Disclosed are improved methods for treating cotton-containing fabrics as well as the fabrics produced from these methods. In particular, the disclosed methods are directed to contacting cotton-containing fabrics with a cellulase solution containing a fungal cellulase composition which is substantially free of all CBH I type cellulase components. Cotton-containing fabrics so treated possess decreased strength loss as compared to fabrics treated with a cellulase solution containing a complete cellulase composition.

10 Claims, 10 Drawing Sheets

OTHER PUBLICATIONS

Miller et al., (1985) Mol. and Cell. Biol., vol. 5(7) pp. 1714–1721.

Ohishi et al., "Reformation of Cotton Fabric by Cellulase".

Penttila et al., (1986) Gene vol. 45, pp. 253–263.

Sambrook et al., (1989) Molecular Cloning A Laboratory Manual 2nd Ed. Cold Spring Harbor Laboratory Press pp. 1.53–1.73.

Schülein (1988) Methods in Enzymology vol. 160, pp. 234–242.

Sheir-Neiss and Montenecourt, (1984) Appl. Microbiol. Biotechnol. vol. 20, pp. 46–53.

Shoemaker et al., (1983) Biotechnology vol. 1, pp. 691–696.

Shoemaker et al., (1983) Biotechnology pp. 687–690.

Yamagishi (1986) The Shizuoka Prefectural Hamamatsu Textile Industrial Research Institute Report vol. 24, pp. 54–61.

Wood (1985) Biochem Soc. Trans vol. 13, pp. 407–410.

Wood et al., (1988) Biochemistry and Genetics of Cellulose Degradation pp. 31–52.

Teeri, *The Cellulolytic Enzyme System of Trichoderma Veesei*, Publications 38, pp. 13,17–20 1987.

Wood et al., Biochem. J., 260, 37–43, Published May 15, 1989.

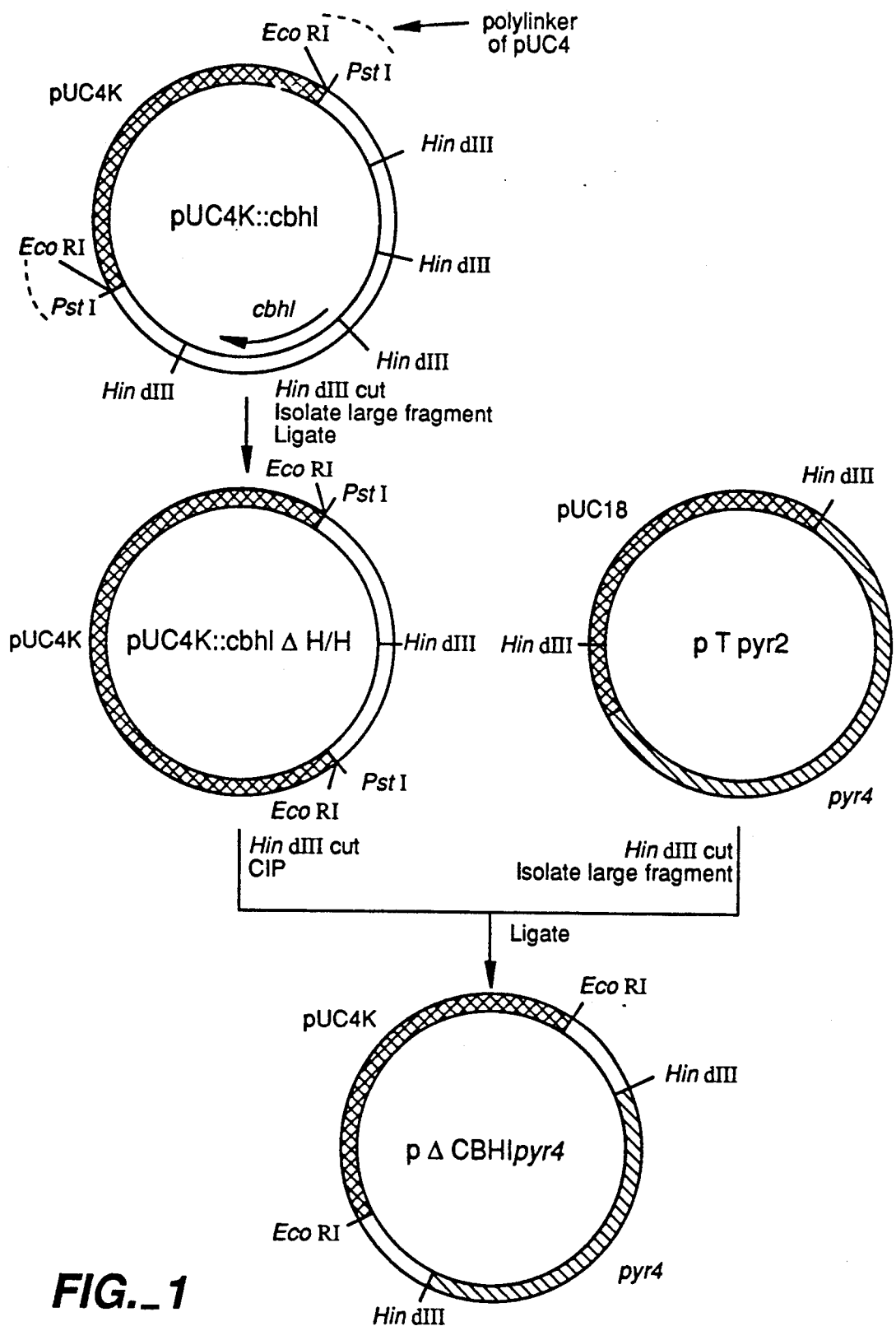
FIG._1

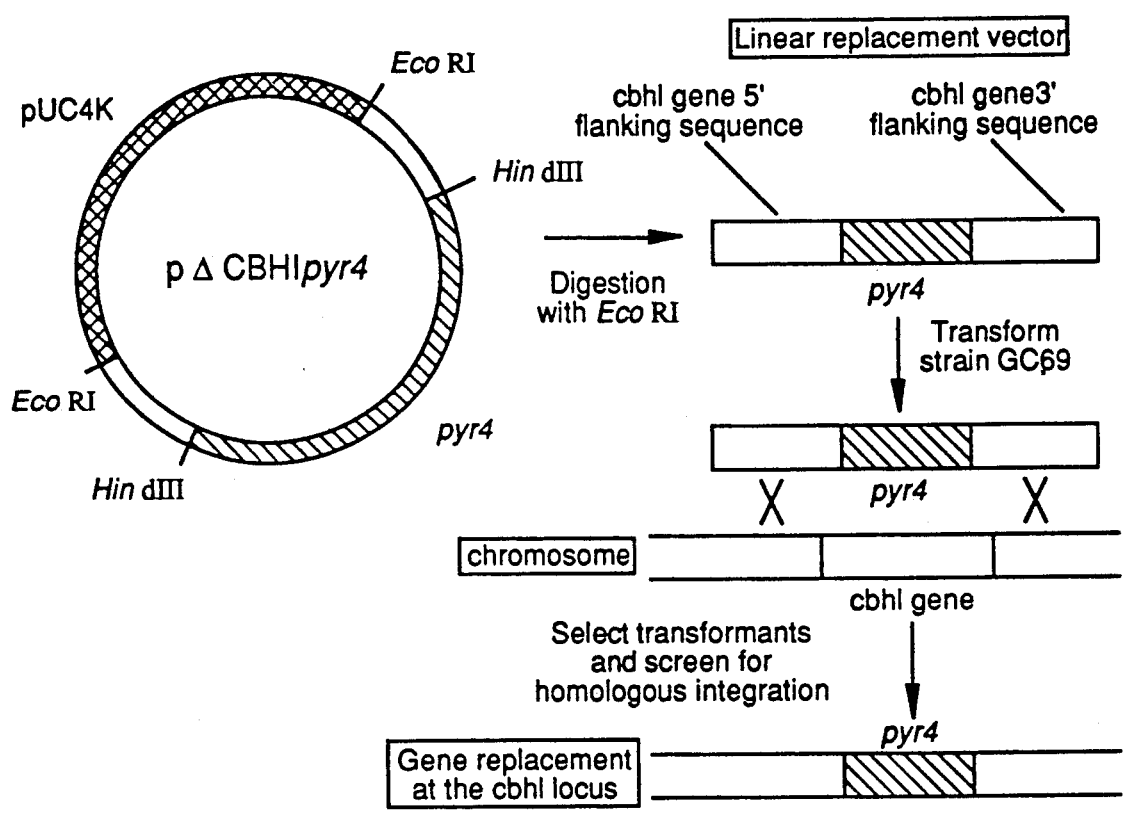
FIG._2

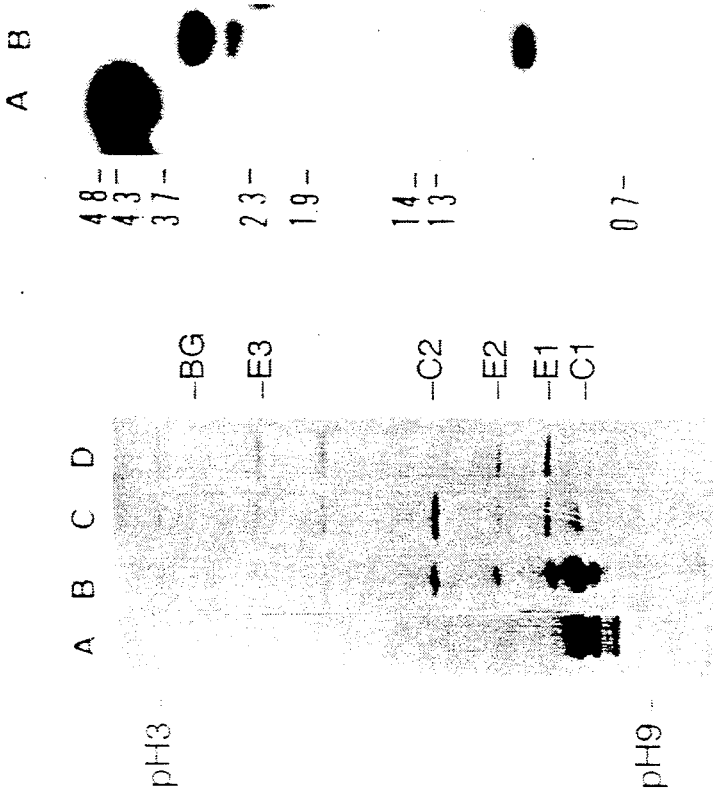
FIG._7
FIG._5
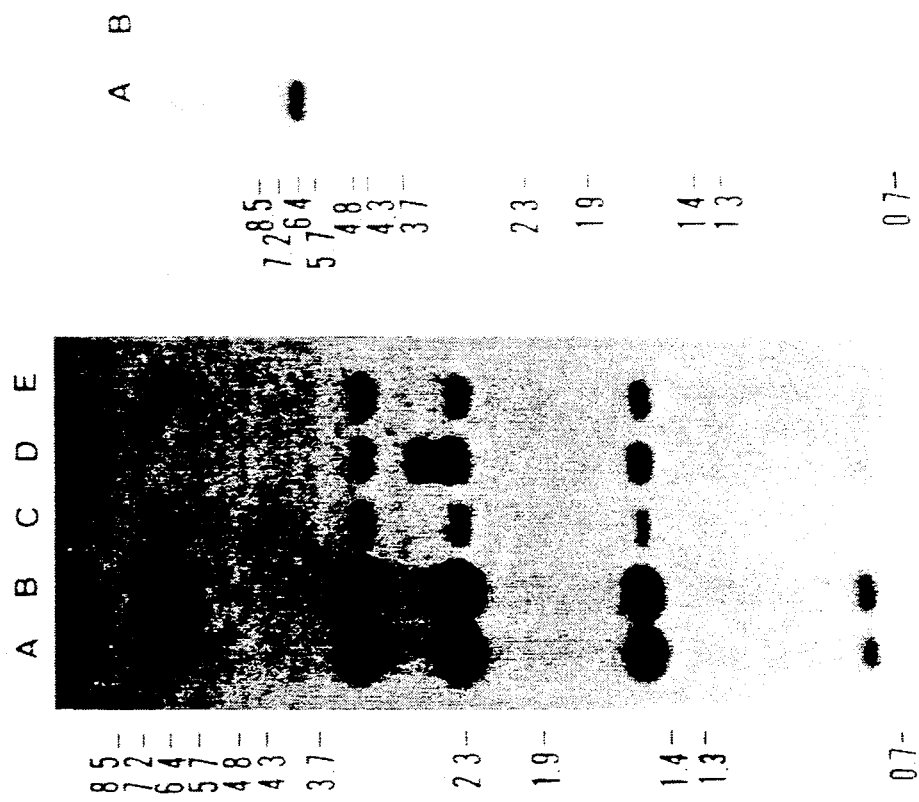
FIG._4
FIG._3

FIG._6A
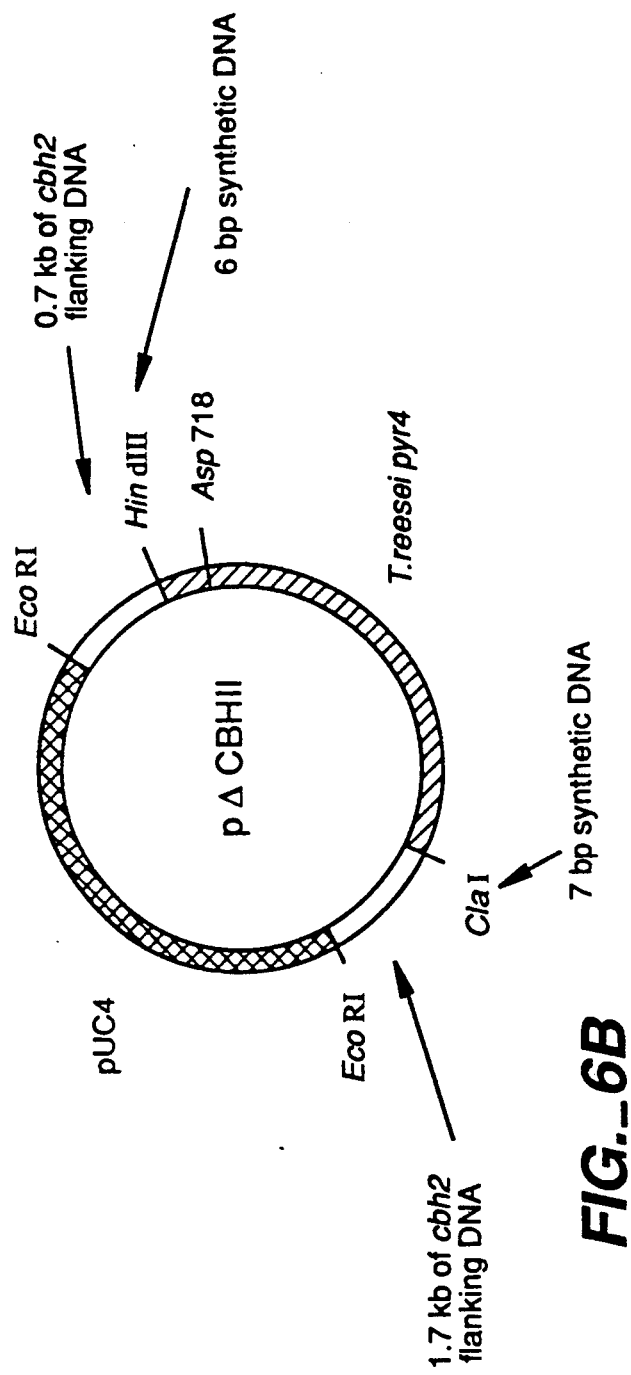
FIG._6B

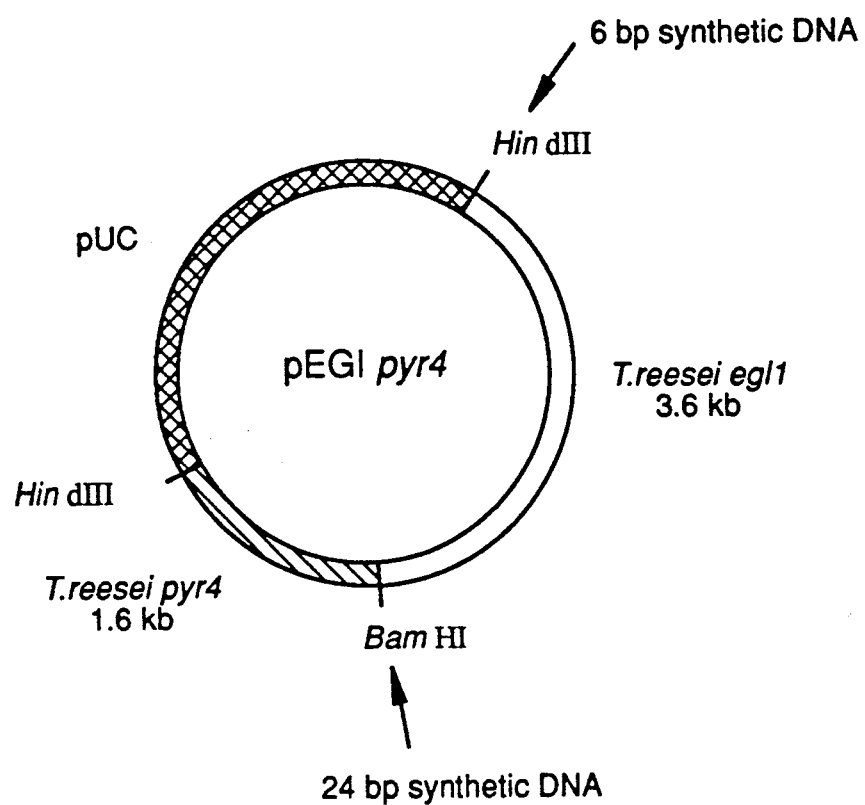
FIG._8

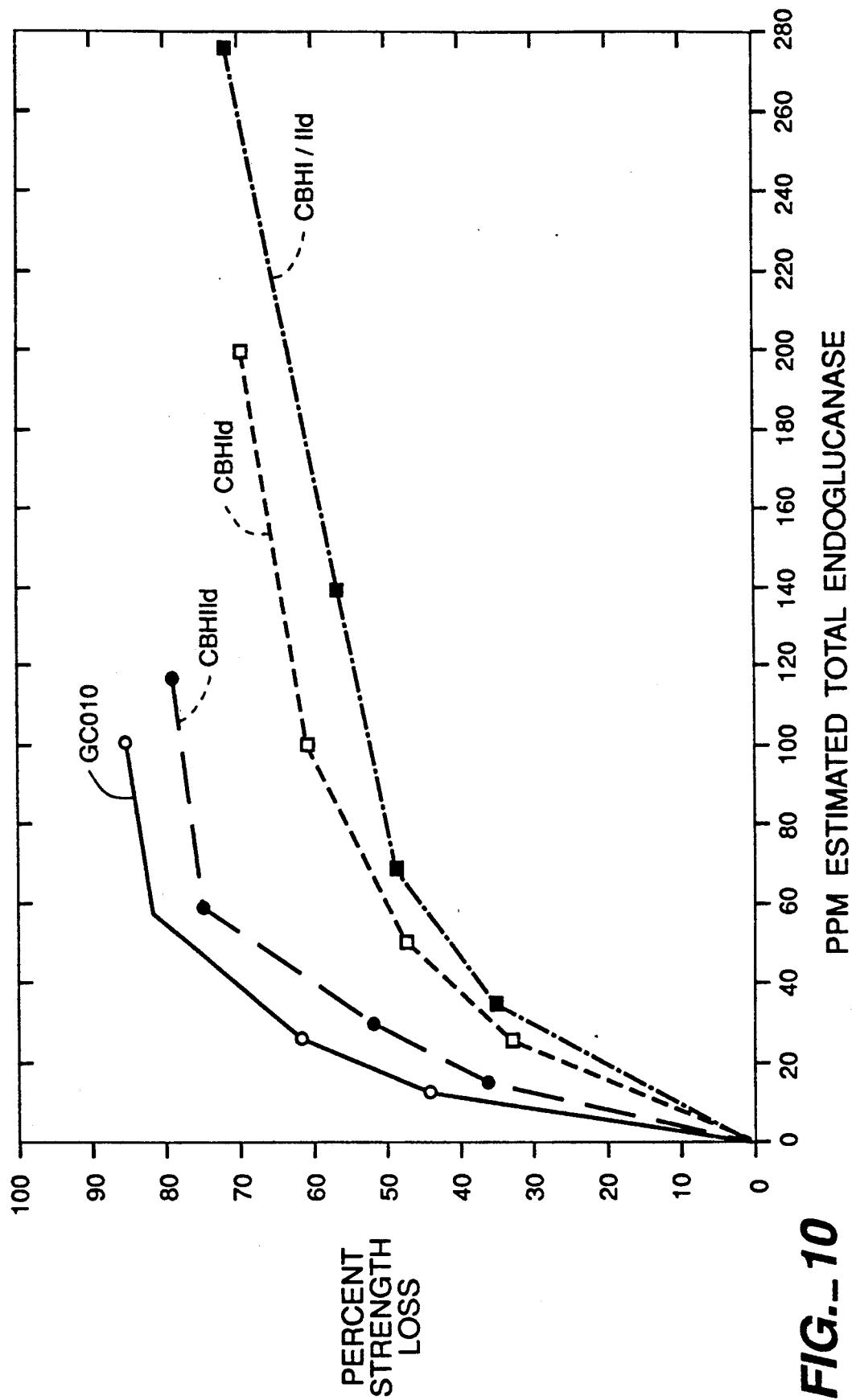
FIG._10

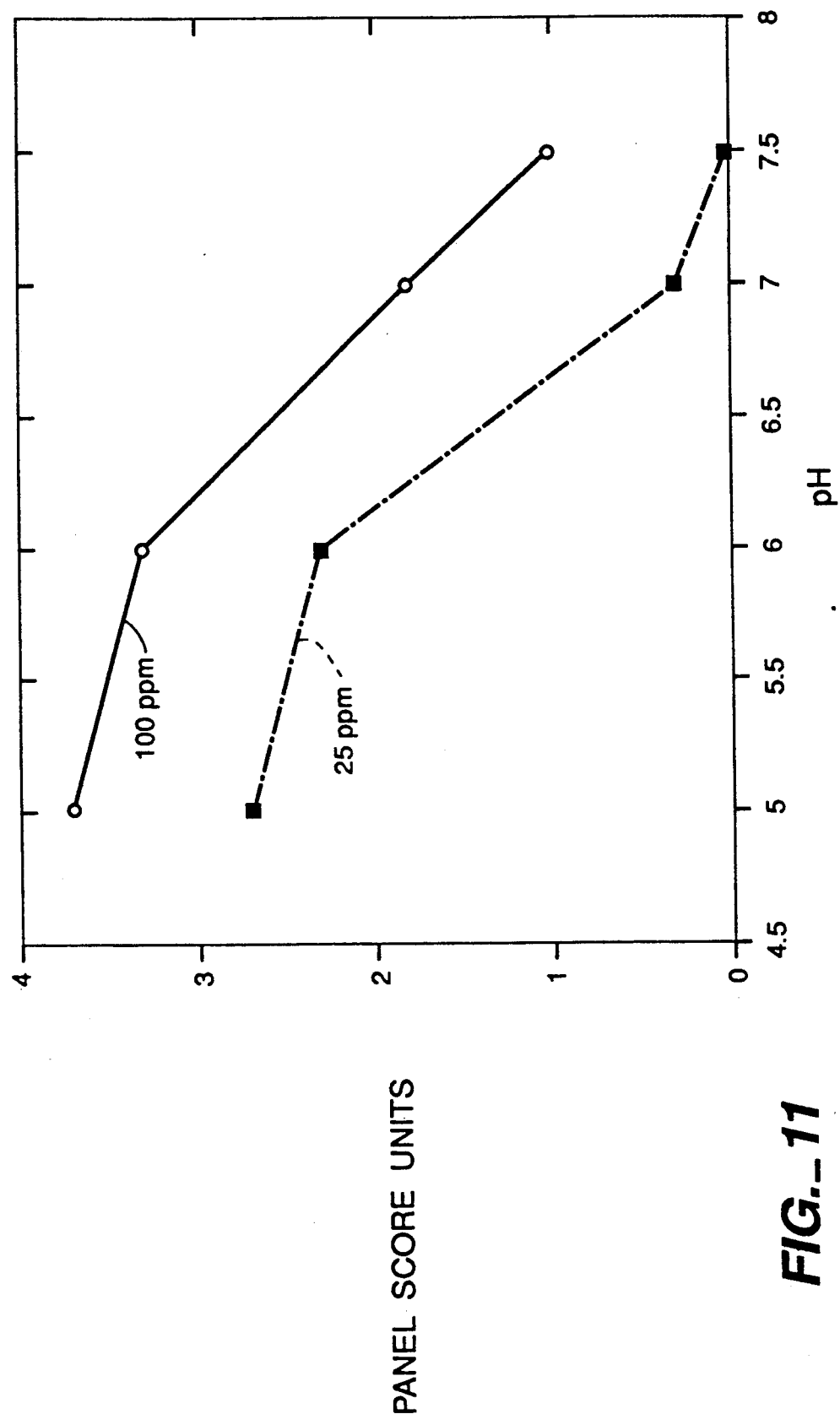
FIG._11

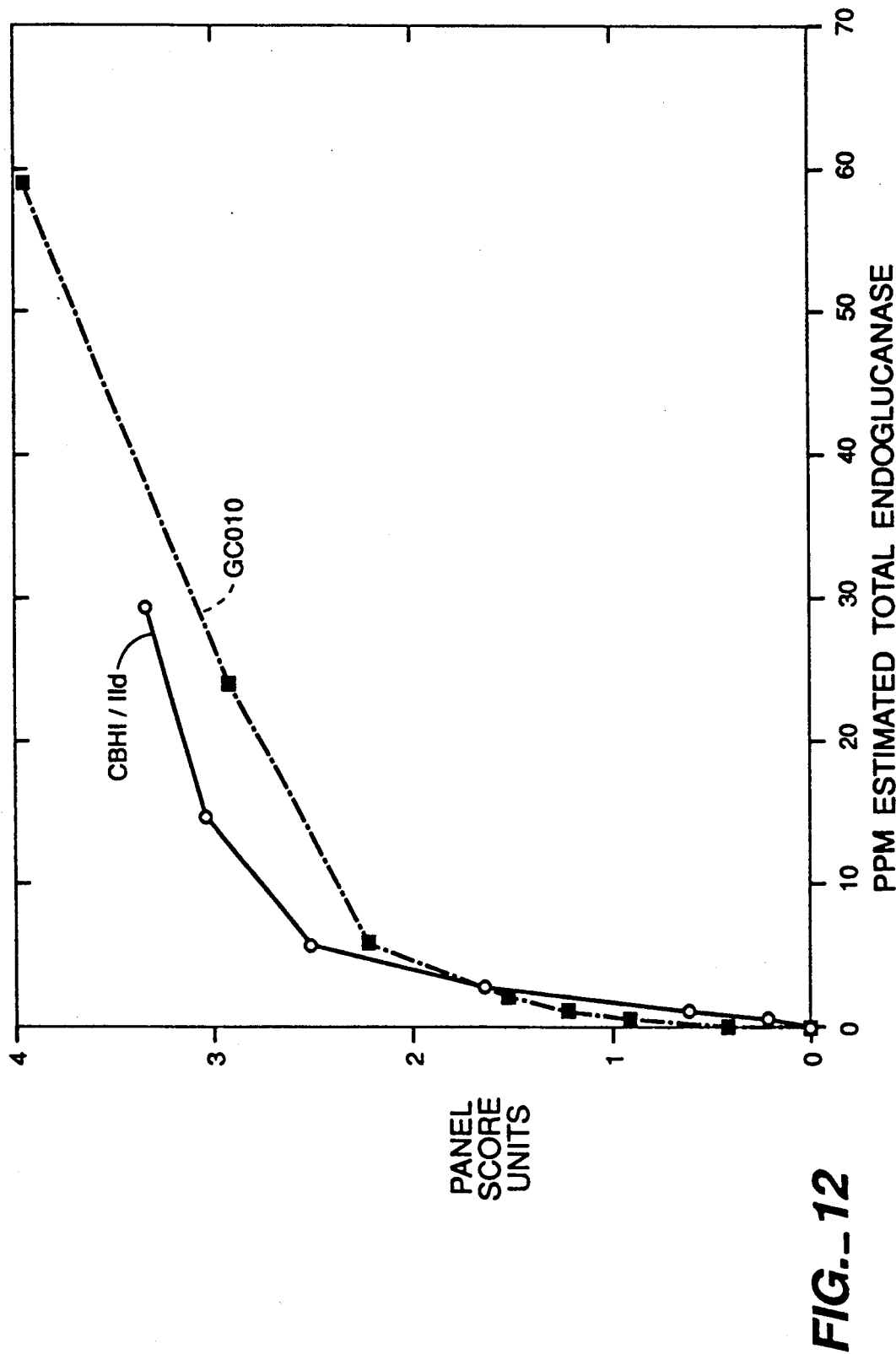
FIG._12

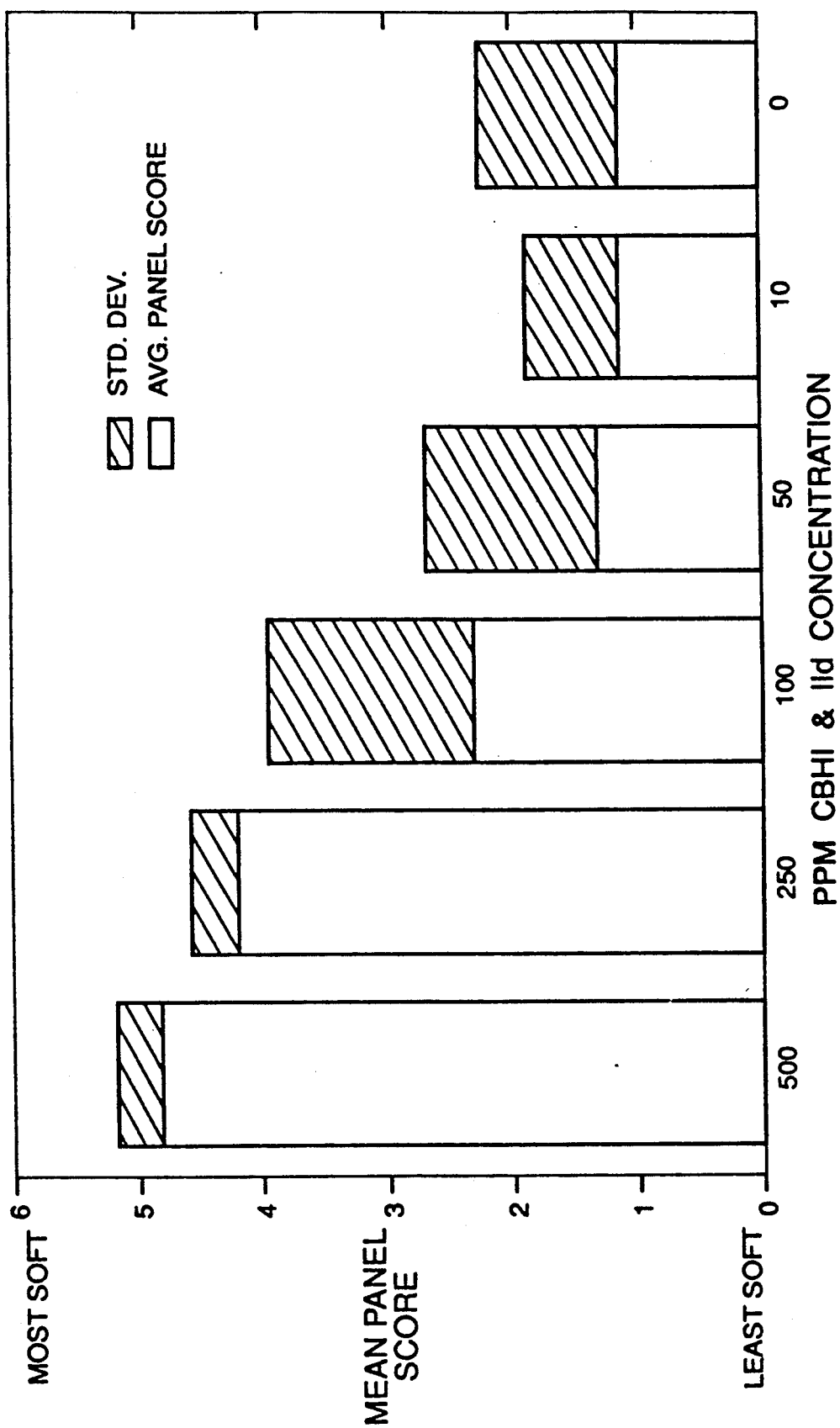
FIG._13

5,246,853

METHOD FOR TREATING COTTON-CONTAINING FABRIC WITH A CELLULASE COMPOSITION CONTAINING ENDOGLUCANASE COMPONENTS AND WHICH COMPOSITION IS FREE OF EXO-CELLOBIOHYDROLASE I

CROSS-REFERENCE TO RELATED APPLICATIONS

This application is a continuation-in-part of U.S. Ser. No. 07/593,919 filed Oct. 5, 1990, now abandoned and which is incorporated herein by reference in its entirety.

BACKGROUND OF THE INVENTION

1. Field of the Invention

The present invention is directed to improved methods for treating cotton-containing fabrics with cellulase as well as the fabrics produced from these methods. In particular, the improved methods of the present invention are directed to contacting cotton-containing fabrics with an aqueous solution containing a fungal cellulase composition substantially free of all CBH I type cellulase components. When the cotton-containing fabric is treated with such solutions, the resulting fabric possesses the expected enhancements in, for example, feel, appearance, and/or softening, etc., as compared to the fabric prior to treatment and the fabric also possesses decreased strength loss as compared to the fabric treated with a cellulase composition containing CBH I type cellulase components.

2. State of the Art

During or shortly after their manufacture, cotton-containing fabrics can be treated with cellulase in order to impart desirable properties to the fabric. For example, in the textile industry, cellulase has been used to improve the feel and/or appearance of cotton-containing fabrics, to remove surface fibers from cotton-containing knits, for imparting a stone washed appearance to cotton-containing denims and the like.

In particular, Japanese Patent Application Nos. 58-36217 and 58-54082 as well as Ohishi et al., "Reformation of Cotton Fabric by Cellulase" and JTN December 1988 journal article "What's New—Weight Loss Treatment to Soften the Touch of Cotton Fabric" each disclose that treatment of cotton-containing fabrics with cellulase results in an improved feel for the fabric. It is generally believed that this cellulase treatment removes cotton fuzzing and/or surface fibers which reduces the weight of the fabric. The combination of these effects imparts improved feel to the fabric, i.e., the fabric feels more like silk.

Additionally, it was heretofore known in the art to treat cotton-containing knitted fabrics with a cellulase solution under agitation and cascading conditions, for example, by use of a jet, for the purpose of removing broken fibers and threads common to these knitted fabrics. When so treated, buffers are generally not employed because they are believed to adversely affect dye shading with selected dyes.

It was still further heretofore known in the art to treat cotton-containing woven fabrics with a cellulase solution under agitation and cascading conditions. When so treated, the cotton-containing woven fabric possesses improved feel and appearance as compared to the fabric prior to treatment.

Lastly, it was also heretofore known that the treatment of cotton-containing dyed denim with cellulase solutions under agitating and cascading conditions, i.e., in a rotary drum washing machine, would impart a "stone washed" appearance to the denim.

A common problem associated with the treatment of such cotton-containing fabrics with a cellulase solution is that the treated fabrics exhibit significant strength loss as compared to the untreated fabric. Strength loss arises because the cellulase hydrolyzes cellulose ($\beta$-1,4-glucan linkages) which, in turn, can result in a breakdown of a portion of the cotton polymer. As more and more cotton polymers are disrupted (broken down), the tensile strength of the fabric is reduced.

Because methods involving agitation and cascading of cellulase solutions over cotton woven fabrics require shorter reaction times, these methods are believed to provide cotton-containing woven fabrics of reduced strength loss as compared to cellulase treatment methods not involving agitation and cascading. In any event, such methods still nevertheless result in significant strength loss.

Accordingly, it would be particularly desirable to modify such cellulase treatment methods so as to provide reduced strength loss while still achieving the desired enhancements in the treated cotton-containing fabric arising from treatment with cellulase as compared to the fabric prior to treatment.

Additionally, because fungal sources of cellulase are known to secrete very large quantities of cellulase and further because fermentation procedures for such fungal sources as well as isolation and purification procedures for isolating the cellulase are well known in the art, it would be particularly advantageous to use such fungal cellulases in the methods for improving feel and/or appearance.

SUMMARY OF THE INVENTION

The present invention is directed to the discovery that heretofore known methods for treating cotton-containing fabrics with fungal cellulases can be improved by employing a fungal cellulase composition which is substantially free of all CBH I type components. Surprisingly, it has been found that EG type components are capable of imparting enhancements to the treated fabric with regard to feel, appearance, softness, color enhancement, and/or stone washed appearance as compared to the fabric before treatment with such a cellulase composition. Additionally, it has been found that it is the CBH I type components in combination with the EG type components which account for a sizable portion of the strength loss in the treated fabric.

In view of the above, in one of its method aspects, the present invention is directed to an improved method for the treatment of cotton-containing fabrics with a fungal cellulase composition wherein said improvement comprises employing a fungal cellulase composition which is substantially free of all CBH I type components. In a preferred embodiment, the fungal cellulase composition is free of all CBH I type and all CBH II type components. In still another preferred embodiment, the fungal cellulase composition comprises at least about 10 weight percent and preferably at least about 20 weight percent of EG type components based on the total weight of protein in the cellulase composition.

In another of its method aspects, the present invention is directed to an improved method for the treatment of cotton-containing fabrics with an aqueous fungal cellulase solution wherein said method is conducted with agitation under conditions so as to produce a cascading effect of the cellulase solution over the fabric wherein said improvement comprises employing a fungal cellulase composition which is substantially free of all CBH I type components. In a preferred embodiment, the fungal cellulase composition is free of all CBH I type components and all CBH II type components. In still another preferred embodiment, the fungal cellulase composition comprises at least about 10 weight percent and preferably at least about 20 weight percent of EG type components based on the total weight of protein in the cellulase composition.

Cotton-containing fabrics treated by the methods of this invention have the expected enhancement(s) as compared to the fabric prior to treatment while exhibiting reduced strength loss as compared to the fabric treated with a fungal cellulase composition which contains CBH I type cellulase components. The reduced strength loss evidences that methods of this invention are strength loss resistant.

In its composition aspects, the present invention is directed to a cotton-containing fabric treated in the methods of this invention as defined above.

BRIEF DESCRIPTION OF THE DRAWINGS

FIG. 1 is an outline of the construction of pΔCBHIpyr4.

FIG. 2 illustrates deletion of the *Trichoderma longibrachiatum* cbh1 gene by integration of the larger EcoRI fragment from pΔCBHIpyr4 at the cbh1 locus on one of the *Trichoderma longibrachiatum* chromosomes.

FIG. 3 is an autoradiograph of DNA from a *Trichoderma longibrachiatum* strain GC69 transformed with EcoRI digested pΔCBHIpyr4 after Southern blot analysis using a $^{32}P$ labelled pΔCBHIpyr4 as the probe.

FIG. 4 is an autoradiograph of DNA from a *Trichoderma longibrachiatum* strain GC69 transformed with EcoRI digested pΔCBHIpyr4 after Southern blot analysis using a $^{32}P$ labelled pIntCBHI as the probe.

FIG. 5 is an isoelectrofocusing gel displaying the proteins secreted by the wild type and by transformed strains of *Trichoderma longibrachiatum*. Specifically, in FIG. 5, Lane A of the isoelectrofocusing gel employs partially purified CBH I from *Trichoderma longibrachiatum*; Lane B employs protein from a wild type *Trichoderma longibrachiatum*; Lane C employs protein from a *Trichoderma longibrachiatum* strain with the cbh1 gene deleted; and Lane D employs protein from a *Trichoderma longibrachiatum* strain with the cbh1 and cbh2 genes deleted.

In FIG. 5, the right hand side of the figure is marked to indicate the location of the single proteins found in one or more of the secreted proteins Specifically, BG refers to β-glucosidase; E1 refers to endoglucanase I; E2 refers to endoglucanase II; E3 refers to endoglucanase III; C1 refers to exo-cellobiohydrolase I; and C2 refers to exo-cellobiohydrolase II.

FIG. 6A is a representation of the *Trichoderma longibrachiatum* cbh2 locus cloned as a 4.1 kB EcoRI fragment of genomic DNA and FIG. 6B is a representation of the cbh2 gene deletion vector, pPΔCBHII.

FIG. 7 is an autoradiograph of DNA from a *Trichoderma longibrachiatum* strain P37PΔCBHI transformed with EcoRI digested pPΔCBHII after Southern blot analysis using a $^{32}P$ labelled pPΔCBHII as the probe.

FIG. 8 is a diagram of the plasmid pEGIpyr4.

FIG. 10 illustrates strength loss results after three wash cycles in a launderometer for cotton-containing fabrics treated with cellulase compositions having varying amounts of CBH components.

FIG. 11 illustrates fiber removal results (based on panel test scores) for cotton-containing fabrics treated with cellulase secreted by a wild type *Trichoderma longibrachiatum* (whole cellulase) at various pHs.

FIG. 12 illustrates fiber removal results (based on panel test scores) for cotton-containing fabrics treated with varying concentrations (in ppm) of cellulase secreted by a wild type *Trichoderma longibrachiatum* and for a cotton fabric treated with cellulase secreted by a strain of *Trichoderma longibrachiatum* genetically engineered so as to be incapable of secreting CBH I and CBH II.

FIG. 13 illustrates the softness panel test results for varying concentrations (in ppm) of an EG enriched cellulase composition derived from a strain of *Trichoderma longibrachiatum* genetically modified so as to be incapable of producing CDH I and II.

DETAILED DESCRIPTION OF THE PREFERRED EMBODIMENTS

Figure 9:
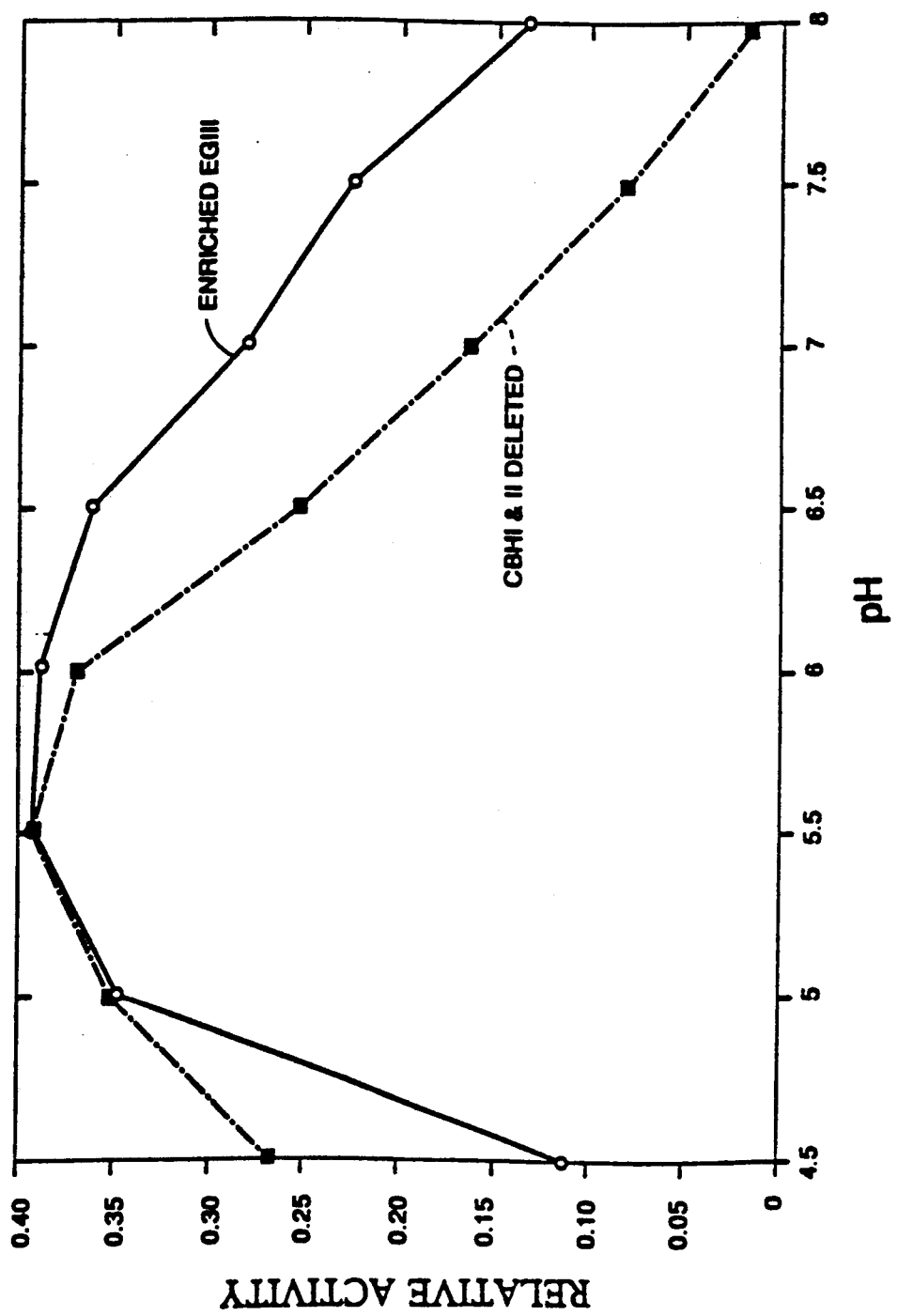
FIG. 9 illustrates the RBB-CMC activity profile of an acidic EG enriched fungal cellulase composition (CBH I and II deleted) derived from *Trichoderma longibrachiatum* over a pH range at 40° C.; as well as the activity profile of an enriched EG III cellulase composition derived from *Trichoderma longibrachiatum* over a pH range at 40° C.

As noted above, the methods of this invention are improvements in prior art methods for treating cotton-containing fabrics with cellulase. The improvement comprises using a specific cellulase composition which imparts the desired enhancement(s) to the fabric while minimizing strength loss in the fabric. However, prior to discussing this invention in detail, the following terms will first be defined.

The term "cotton-containing fabric" refers to sewn or unsewn fabrics made of pure cotton or cotton blends including cotton woven fabrics, cotton knits, cotton denims, cotton yarns and the like. When cotton blends are employed, the amount of cotton in the fabric should be at least about 40 percent by weight cotton; preferably, more than about 60 percent by weight cotton; and most preferably, more than about 75 percent by weight cotton. When employed as blends, the companion material employed in the fabric can include one or more non-cotton fibers including synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers. It is contemplated that regenerated cellulose, such as rayon, could be used as a substitute for cotton in the methods of this invention.

The term "finishing" as employed herein means the application of a sufficient amount of finish to a cotton-containing fabric so as to substantially prevent cellulolytic activity of the cellulase on the fabric. Finishes are generally applied at or near the end of the manufacturing process of the fabric for the purpose of enhancing the properties of the fabric, for example, softness, drapability, etc., which additionally protects the fabric from reaction with cellulases. Finishes useful for finishing a cotton-containing fabric are well known in the art and include resinous materials, such as melamine, glyoxal, or ureaformaldehyde, as well as waxes, silicons, fluorochemicals and quaternaries. When so finished, the cotton-containing fabric is substantially less reactive to cellulase.

The term "fungal cellulase" refers to the enzyme composition derived from fungal sources or microorganisms genetically modified so as to incorporate and express all or part of the cellulase genes obtained from a fungal source. Fungal cellulases act on cellulose and its derivatives to hydrolyze cellulose and give primary products, glucose and cellobiose. Fungal cellulases are distinguished from cellulases produced from non-fungal sources including microorganisms such as actinomycetes, gliding bacteria (myxobacteria) and true bacteria. Fungi capable of producing cellulases useful in preparing cellulase compositions described herein are disclosed in British Patent No. 2 094 826A, the disclosure of which is incorporated herein by reference.

Most fungal cellulases generally have their optimum activity in the acidic or neutral pH range although some fungal cellulases are known to possess significant activity under neutral and slightly alkaline conditions, i.e., for example, cellulase derived from *Humicola insolens* is known to have activity in neutral to slightly alkaline conditions.

Fungal cellulases are known to be comprised of several enzyme classifications having different substrate specificity, enzymatic action patterns, and the like. Additionally, enzyme components within each classification can exhibit different molecular weights, different degrees of glycosylation, different isoelectric points, different substrate specificity, etc. For example, fungal cellulases can contain cellulase classifications which include endoglucanases (EGs), exo-cellobiohydrolases (CBHs), β-glucosidases (BGs), etc. On the other hand, while bacterial cellulases are reported in the literature as containing little or no CBH components, there are a few cases where CBH-like components derived from bacterial cellulases have been reported to possess exo-cellobiohydrolase activity.

A fungal cellulase composition produced by a naturally occurring fungal source and which comprises one or more CBH and EG components wherein each of these components is found at the ratio produced by the fungal source is sometimes referred to herein as a "complete fungal cellulase system" or a "complete fungal cellulase composition" to distinguish it from the classifications and components of cellulase isolated therefrom, from incomplete cellulase compositions produced by bacteria and some fungi, or from a cellulase composition obtained from a microorganism genetically modified so as to overproduce, underproduce, or not produce one or more of the CBH and/or EG components of cellulase.

The fermentation procedures for culturing fungi for production of cellulase are known per se in the art. For example, cellulase systems can be produced either by solid or submerged culture, including batch, fed-batch and continuous-flow processes. The collection and purification of the cellulase systems from the fermentation broth can also be effected by procedures known per se in the art.

"Endoglucanase ("EG") type components" refer to all of those fungal cellulase components or combination of components which exhibit textile activity properties similar to the endoglucanase components of *Trichoderma longibrachiatum*. In this regard, the endoglucanase components of *Trichoderma longibrachiatum* (specifically, EG I, EG II, EG III, and the like either alone or in combination) impart improved feel, improved appearance, softening, color enhancement, and/or a stone washed appearance to cotton-containing fabrics (as compared to the fabric prior to treatment) when these components are incorporated into a textile treatment medium and the fabric is treated with this medium. Additionally, treatment of cotton-containing fabrics with endoglucanase components of *Trichoderma longibrachiatum* results in less strength loss as compared to the strength loss arising from treatment with a similar composition but which additionally contains CBH I type components.

Accordingly, endoglucanase type components are those fungal cellulase components which impart improved feel, improved appearance, softening, color enhancement, and/or a stone washed appearance to cotton-containing fabrics (as compared to the fabric before treatment) when these components are incorporated into a medium used to treat the fabrics and which impart reduced strength loss to cotton-containing fabrics as compared to the strength loss arising from treatment with a similar cellulase composition but which additionally contains CBH I type components.

Such endoglucanase type components may not include components traditionally classified as endoglucanases using activity tests such as the ability of the component (a) to hydrolyze soluble cellulose derivatives such as carboxymethylcellulose (CMC), thereby reducing the viscosity of CMC containing solutions, (b) to readily hydrolyze hydrated forms of cellulose such as phosphoric acid swollen cellulose (e.g., Walseth cellulose) and hydrolyze less readily the more highly crystalline forms of cellulose (e.g., Avicel, Solkafloc, etc.). On the other hand, it is believed that not all endoglucanase components, as defined by such activity tests, will impart one or more of the enhancements to cotton-containing fabrics as well as reduced strength loss to cotton-containing fabrics. Accordingly, it is more accurate for the purposes herein to define endoglucanase type components as those components of fungal cellulase which possess similar textile activity properties as possessed by the endoglucanase components of *Trichoderma longibrachiatum*.

Fungal cellulases can contain more than one EG type component. The different components generally have different isoelectric points, different molecular weights, different degrees of glycosylation, different substrate specificity, different enzymatic action patterns, etc. The different isoelectric points of the components allow for their separation via ion exchange chromatography and the like. In fact, the isolation of components from different fungal sources is known in the art. See, for example, Bjork et al., U.S. Ser. No. 07/686,265 which is a continuation of U.S. Ser. No. 07/422,814 which is now abandoned. Schulein et al., International Application WO 89/09259, Wood et al., Biochemistry and Genetics of Cellulose Degradation, pp. 31 to 52 (1988); Bhat et al., Carbohydrate Research, Vol. 190, pp. 279 to 297 (1989); Schulein, Methods in Enzymology, Vol. 160, pp. 234 to 242 (1988); and the like. The entire disclosure of each of these references is incorporated herein by reference.

In general, it is contemplated that combinations of EG type components may give a synergistic response in imparting enhancements to the cotton-containing fabrics as well as imparting reduced strength loss as compared to a single EG component. On the other hand, a single EG type component may be more stable or have a broader spectrum of activity over a range of pHs. Accordingly, the EG type components employed in this invention can be either a single EG type component or a combination of two or more EG type components. When a combination of components is employed, the EG type component may be derived from the same or different fungal sources.

It is contemplated that EG type components can be derived from bacterially derived cellulases.

"Exo-cellobiohydrolase type ("CBH type") components" refer to those fungal cellulase components which exhibit textile activity properties similar to CBH I and/or CBH II cellulase components of *Trichoderma longibrachiatum*. In this regard, when used in the absence of EG type cellulase components (as defined above), the CBH I and CBH II components of *Trichoderma longibrachiatum* alone do not impart any significant enhancements in feel, appearance, color enhancement and/or stone washed appearance to the so treated cotton-containing fabrics. Additionally, when used in combination with EG type components, the CBH I component of *Trichoderma longibrachiatum* imparts enhanced strength loss to the cotton-containing fabrics.

Accordingly, CBH I type components and CBH II type components refer to those fungal cellulase components which exhibit textile activity properties similar to CBH I and CBH II components of *Trichoderma longibrachiatum*, respectively. As noted above, for CBH I type components, this includes the property of enhancing strength loss of cotton-containing fabrics when used in the presence of EG type components. In a preferred embodiment and when used in combination with EG type components, the CBH I type components of *Trichoderma longibrachiatum* can impart an incremental cleaning benefit. Additionally, it is contemplated that the CBH I components of *Trichoderma longibrachiatum* when used alone or in combination with EG type components, can impart an incremental softening benefit.

Such exo-cellobiohydrolase type components could possibly not include components traditionally classed as exo-cellobiohydrolases using activity tests such as those used to characterize CBH I and CBH II from *Trichoderma longibrachiatum*. For example, such components (a) are competitively inhibited by cellobiose ($K_i$ approximately 1 mM); (b) are unable to hydrolyze to any significant degree substituted celluloses, such as carboxymethylcellulose, etc., and (c) hydrolyze phosphoric acid swollen cellulose and to a lesser degree highly crystalline cellulose. On the other hand, it is believed that some fungal cellulase components which are characterized as CBH components by such activity tests, will impart improved feel, appearance, softening, color enhancement, and/or a stone washed appearance to cotton-containing fabrics with minimal strength loss when used alone in the cellulase composition. Accordingly, it is believed to be more accurate for the purposes herein to define such exo-cellobiohydrolases as EG type components because these components possess similar functional properties in textile uses as possessed by the endoglucanase components of *Trichoderma longibrachiatum*.

Fungal cellulases substantially free of all CBH I type components can be obtained by purification techniques. Specifically, the complete cellulase system can be purified into substantially pure components by recognized separation techniques well published in the literature, including ion exchange chromatography at a suitable pH, affinity chromatography, size exclusion and the like. For example, in ion exchange chromatography (usually anion exchange chromatography), it is possible to separate the cellulase components by eluting with a pH gradient, or a salt gradient, or both a pH and a salt gradient. As used herein, the term "cellulase composition substantially free of all CBH I type cellulase components" means that the cellulase composition, based on the weight of protein, will contain less than 1 weight percent CBH I type cellulase components.

It is also contemplated that cellulase compositions substantially free of all CBH I type components can be prepared by means other than isolation and recombination of the components. For example, recombinant techniques can be used to prepare microorganisms which are incapable of producing any CBH I type components or which are incapable of producing any CBH type components.

In regard to the above, a preferred method for the preparation of cellulase compositions substantially free of CBH I type components is by genetically modifying a microorganism so as to be incapable of expressing CBH I type components which methods do not express any heterologous protein. Likewise, it is also possible to genetically modify a microorganism so as to additionally overexpress one or more EG type components. For example, U.S. Ser. No. 07/593,919, filed Oct. 5, 1990 and which is incorporated herein by reference in its entirety, discloses methods for genetically engineering *Trichoderma longibrachiatum* so as to be incapable of expressing one or more CBH components and/or overexpressing one or more EG components. Moreover, the methods of that application create *Trichoderma longibrachiatum* strains which do not express any heterologous proteins. Likewise, Miller et al., "Direct and Indirect Gene Replacement in *Aspergillus nidulans*", Molecular and Cellular Biology, p. 1714–1721 (1985) discloses methods for deleting genes in *Aspergillus nidulans* by DNA mediated transformation using a linear fragment of homologous DNA. The methods of Miller et al., would achieve gene deletion without producing any heterologous proteins.

In view of the above, the deletion of the genes responsible for producing CBH I type and/or CBH II type cellulase components would also have the effect of enriching the amount of EG type components present in the cellulase composition. Likewise, the deletion of those genes responsible for producing CBH I and II type components would result in a cellulase composition free of CBH type components.

It is still further contemplated that fungal cellulase compositions can be used herein from fungal sources which produce an incomplete fungal cellulase composition. For example, it is known that certain fungi produce cellulase compositions free of CBH components. See, for example, Coughlan et al., Biochemistry and Genetics of Cellulose Degradation, Aubert et al. Editors, pp. 11–30 (Academic Press, 1988), disclose that brown rot fungi do not apparently produce CBH components, but it may be possible that one or more of these components are CBH I type components.

"$\beta$-Glucosidase (BG) components" refer to those components of cellulase which exhibit BG activity; that is to say that such components will act from the non-reducing end of cellobiose and other soluble cellooligosaccharides ("cellobiose") and give glucose as the sole product. BG components do not adsorb onto or react with cellulose polymers. Furthermore, such BG components are competitively inhibited by glucose ($K_i$ approximately 1 mM). While in a strict sense, BG components are not literally cellulases because they cannot degrade cellulose, such BG components are included within the definition of the cellulase system because these enzymes facilitate the overall degradation of cellulose by further degrading the inhibitory cellulose degradation products (particularly cellobiose) produced by the combined action of CBH components and EG components. Without the presence of BG components, moderate or little hydrolysis of crystalline cellulose will occur. BG components are often characterized on aryl substrates such as p-nitrophenol B-D-glucoside (PNPG) and thus are often called aryl-glucosidases. It should be noted that not all aryl glucosidases are BG components, in that some do not hydrolyze cellobiose.

It is contemplated that the presence or absence of BG components in the cellulase composition can be used to regulate the activity of any CBH components in the composition (i.e., non-CBH I type components). Specifically, because cellobiose is produced during cellulose degradation by CBH components, and because high concentrations of cellobiose are known to inhibit CBH activity, and further because such cellobiose is hydrolyzed to glucose by BG components, the absence of BG components in the cellulase composition will "turn-off" CBH activity when the concentration of cellobiose reaches inhibitory levels. It is also contemplated that one or more additives (e.g., cellobiose, glucose, etc.) can be added to the cellulase composition to effectively "turn-off", directly or indirectly, CBH I type activity as well as other CBH activity. When such additives are employed, the resulting composition is considered to be a composition free of all CBH I type components if the amount of additive is sufficient to result in effectively no CBH I type activity.

On the other hand, a cellulase composition containing added amounts of BG components may increase overall hydrolysis of cellulose if the level of cellobiose generated by the CBH components becomes restrictive of such overall hydrolysis in the absence of added BG components.

Methods to either increase or decrease the amount of BG components in the cellulase composition are disclosed in U.S. Ser. No. 07/625,140, filed Dec. 10, 1990, and entitled "SACCHARIFICATION OF CELLULOSE BY CLONING AND AMPLIFICATION OF THE β-GLUCOSIDASE GENE BY *TRICHODERMA LONGIBRACHIATUM*," which application is incorporated herein by reference in its entirety.

Fungal cellulases can contain more than one BG component. The different components generally have different isoelectric points which allow for their separation via ion exchange chromatography and the like. Either a single BG component or a combination of BG components can be employed.

When employed in textile treatment solutions, the BG component is generally added in an amount sufficient to prevent inhibition by cellobiose of any CBH and EG components found in the cellulase composition. The amount of BG component added depends upon the amount of cellobiose produced in the textile composition which can be readily determined by the skilled artisan. However, when employed, the weight percent of BG component relative to any CBH type components present in the cellulase composition is preferably from about 0.2 to about 10 weight percent and more preferably, from about 0.5 to about 5 weight percent.

Preferred fungal cellulases for use in preparing the fungal cellulase compositions used in this invention, are those obtained from *Trichoderma longibrachiatum, Trichoderma koningii, Pencillum sp., Humicola insolens*, and the like. Certain fungal cellulases are commercially available, i.e., CELLUCAST (available from Novo Industry, Copenhagen, Denmark), RAPIDASE (available from Gist Brocades, N.V., Delft, Holland), CYTOLASE 123 (available from Genencor International, South San Francisco, Calif.) and the like. Other fungal cellulases can be readily isolated by art recognized fermentation and isolation procedures.

The term "buffer" refers to art recognized acid/base reagents which stabilize the cellulase solution against undesired pH shifts during the cellulase treatment of the cotton-containing fabric. In this regard, it is art recognized that cellulase activity is pH dependent. That is to say that a specific cellulase composition will exhibit cellulolytic activity within a defined pH range with optimal cellulolytic activity generally being found within a small portion of this defined range. The specific pH range for cellulolytic activity will vary with each cellulase composition. As noted above, while most cellulases will exhibit cellulolytic activity within an acidic to neutral pH profile, there are some cellulase compositions which exhibit cellulolytic activity in an alkaline pH profile.

During cellulase treatment of the cotton-containing fabric, it is possible that the pH of the initial cellulase solution could be outside the range required for cellulase activity. It is further possible for the pH to change during treatment of the cotton-containing fabric, for example, by the generation of a reaction product which alters the pH of the solution. In either event, the pH of an unbuffered cellulase solution could be outside the range required for cellulolytic activity. When this occurs, undesired reduction or cessation of cellulolytic activity in the cellulase solution occurs. For example, if a cellulase having an acidic activity profile is employed in a neutral unbuffered aqueous solution, then the pH of the solution will result in lower cellulolytic activity and possibly in the cessation of cellulolytic activity. On the other hand, the use of a cellulase having a neutral or alkaline pH profile in a neutral unbuffered aqueous solution should initially provide significant cellulolytic activity.

In view of the above, the pH of the cellulase solution should be maintained within the range required for cellulolytic activity. One means of accomplishing this is by simply monitoring the pH of the system and adjusting the pH as required by the addition of either an acid or a base. However, in a preferred embodiment, the pH of the system is preferably maintained within the desired pH range by the use of a buffer in the cellulase solution. In general, a sufficient amount of buffer is employed so as to maintain the pH of the solution within the range wherein the employed cellulase exhibits its activity. Insofar as different cellulase compositions have different pH ranges for exhibiting cellulase activity, the specific buffer employed is selected in relationship to the specific cellulase composition employed.

The buffer(s) selected for use with the cellulase composition employed can be readily determined by the skilled artisan taking into account the pH range and optimum for the cellulase composition employed as well as the pH of the cellulase solution. Preferably, the buffer employed is one which is compatible with the cellulase composition and which will maintain the pH of the cellulase solution within the pH range required for optimal activity. Suitable buffers include sodium citrate, ammonium acetate, sodium acetate, disodium phosphate, and any other art recognized buffers.

The tensile strength of cotton-containing fabrics can be measured in a warp and fill direction which are at right angles to each other. Accordingly, the term "warp tensile strength" as used herein refers to the tensile strength of the cotton-containing fabric as measured along the length of the cotton-containing fabric whereas the term "fill tensile strength" refers to the tensile strength of the cotton-containing fabric as measured across the width of the cotton-containing fabric. The tensile strength of the resulting cotton-containing fabric treated with a cellulase solution is compared to its tensile strength prior to treatment with the cellulase solution so as to determine the strength reducing effect of the treatment. If the tensile strength is reduced too much, the resulting cotton-containing fabric will easily tear and/or form holes. Accordingly, it is desirable to maintain a tensile strength (both warp and fill) after treatment which is at least about 50% of the tensile strength before treatment.

The tensile strength of cotton-containing fabrics is readily conducted following ASTM D1682 test methodology. Equipment suitable for testing the tensile strength of such fabrics include a Scott tester or an Instron tester, both of which are commercially available. In testing the tensile strength of cotton-containing fabrics which have been treated with cellulase solutions, care should be taken to prevent fabric shrinkage after treatment and before testing. Such shrinkage would result in erroneous tensile strength data.

Enhancements to the cotton-containing fabric is achieved by those methods heretofore used. For example, cotton-containing fabrics having improved feel can be achieved as per Japanese Patent Application Nos. 58-36217 and 58-54082 as well as Ohishi et al., "Reformation of Cotton Fabric by Cellulase" and JTN December 1988 journal article "What's New—Weight Loss Treatment to Soften the Touch of Cotton Fabric". The teachings of each of these references is incorporated herein by reference.

Similarly, methods for improving both the feel and appearance of cotton-containing fabrics include contacting the fabric with an aqueous solution containing cellulase under conditions so that the solution is agitated and so that a cascading effect of the cellulase solution over the cotton-containing fabric is achieved. Such methods result in improved feel and appearance of the so treated cotton-containing fabric and are described in U.S. Ser. No. 07/598,506, filed Oct. 16, 1990 and which is incorporated herein by reference in its entirety.

Methods for the enhancement of cotton containing knits are described in International Textile Bulletin, Dyeing/Printing/Finishing, pages 5 et seq., $2^{nd}$ Quarter, 1990, which is incorporated herein by reference.

Likewise, methods for imparting a stone washed appearance to cotton-containing denims are described in U.S. Pat. No. 4,832,864, which is incorporated herein by reference in its entirety.

Other methods for enhancing cotton-containing fabrics by treatment with a cellulase composition are known in the art. Preferably, in such methods, the treatment of the cotton-containing fabric with cellulase is conducted prior to finishing the cotton-containing fabric.

As noted above, the present invention is an improvement over prior art methods for treating cotton-containing fabrics insofar as the present invention employs a specific cellulase composition which minimizes strength loss in the treated fabric. The cellulase composition employed herein is a fungal cellulase composition substantially free of CBH I type components and preferably, substantially free of all CBH type components.

Additionally, the use of the cellulase compositions described herein also result in fabric/color enhancement of stressed cotton-containing fabrics. Specifically, during the manufacture of cotton-containing fabrics, the fabric can become stressed and when so stressed, it will contain broken and disordered fibers. Such fibers detrimentally impart a worn and dull appearance to the fabric. However, when treated in the method of this invention, the so stressed fabric is subject to fabric/color enhancement. This is believed to arise by removal of some of the broken and disordered fibers which has the effect of restoring the appearance of the fabric prior to becoming stressed.

Additionally, it is contemplated that by employing the cellulase composition described herein with pigment type dyed fabrics (e.g., denims), these cellulase compositions will cause less redeposition of dye. It is also contemplated that these anti-redeposition properties can be enhanced for one or more specific EG type component(s) as compared to other components.

The fungal cellulase compositions described above are employed in an aqueous solution which contains cellulase and other optional ingredients including, for example, a buffer, a surfactant, a scouring agent, and the like. The concentration of the cellulase composition employed in this solution is generally a concentration sufficient for its intended purpose. That is to say that an amount of the cellulase composition is employed to provide the desired enhancement(s) to the cotton-containing fabric. The amount of the cellulase composition employed is also dependent on the equipment employed, the process parameters employed (the temperature of the cellulase solution, the exposure time to the cellulase solution, and the like), the cellulase activity (e.g., a cellulase solution will require a lower concentration of a more active cellulase composition as compared to a less active cellulase composition), and the like. The exact concentration of the cellulase composition can be readily determined by the skilled artisan based on the above factors as well as the desired effect. Preferably, the concentration of the cellulase composition in the cellulase solution employed herein is from about 0.01 gram/liter of cellulase solution to about 10.0 grams/liter of cellulase solution; and more preferably, from about 0.05 grams/liter of cellulase solution to about 2 gram/liter of cellulase solution. (The cellulase concentration recited above refers to the weight of total protein).

When a buffer is employed in the cellulase solution, the concentration of buffer in the aqueous cellulase solution is that which is sufficient to maintain the pH of the solution within the range wherein the employed cellulase exhibits activity which, in turn, depends on the nature of the cellulase employed. The exact concentration of buffer employed will depend on several factors which the skilled artisan can readily take into account. For example, in a preferred embodiment, the buffer as well as the buffer concentration are selected so as to maintain the pH of the cellulase solution within the pH range required for optimal cellulase activity. In general, buffer concentration in the cellulase solution is about 0.005N and greater. Preferably, the concentration of the buffer in the cellulase solution is from about 0.01 to about 0.5N, and more preferably, from about 0.05 to about 0.15N. It is possible that increased buffer concentrations in the cellulase solution may enhance the rate of tensile strength loss of the treated fabric.

In addition to cellulase and a buffer, the cellulase solution can optionally contain a small amount of a surfactant, i.e., less than about 2 weight percent, and preferably from about 0.01 to about 2 weight percent. Suitable surfactants include any surfactant compatible with the cellulase and the fabric including, for example, anionic, non-ionic and ampholytic surfactants.

Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3.

Ampholytic surfactants include quaternary ammonium salt sulfonates, betaine-type ampholytic surfactants, and the like. Such ampholytic surfactants have both the positive and negative charged groups in the same molecule.

Nonionic surfactants generally comprise polyoxyalkylene ethers, as well as higher fatty acid alkanolamides or alkylene oxide adduct thereof, fatty acid glycerine monoesters, and the like.

Mixtures of such surfactants can also be used.

The liquor ratios, i.e., the ratio of weight of cellulase solution to the weight of fabric, employed herein is generally an amount sufficient to achieve the desired enhancement in the cotton-containing fabric and is dependent upon the process used and the enhancement to be achieve. Preferably, the liquor ratios are generally from about 0.1:1 and greater, and more preferably greater than about 1:1 and even more preferably greater than about 10:1. Use of liquor ratios of greater than about 50:1 are usually not preferred from an economic viewpoint.

Reaction temperatures for cellulase treatment are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 30° C. and greater. Secondly, cellulase is a protein which loses activity beyond a given reaction temperature which temperature is dependent on the nature of the cellulase used. Thus, if the reaction temperature is permitted to go too high, then the cellulolytic activity is lost as a result of the denaturing of the cellulase. As a result, the maximum reaction temperatures employed herein are generally about 65° C. In view of the above, reaction temperatures are generally from about 30° C. to about 65° C.; preferably, from about 35° C. to about 60° C.; and more preferably, from about 35° C. to about 50° C.

Reaction times are generally from about 0.1 hours to about 24 hours and, preferably, from about 0.25 hours to about 5 hours.

The cotton-containing fabrics treated in the methods described above using such cellulase compositions possess reduced strength loss as compared to the same cotton-containing fabric treated in the same manner with a complete fungal cellulase composition.

In a preferred embodiment, a concentrate can be prepared for use in the methods described herein. Such concentrates would contain concentrated amounts of the cellulase composition described above, buffer and surfactant, preferably in an aqueous solution. When so formulated, the concentrate can readily be diluted with water so as to quickly and accurately prepare cellulase solutions having the requisite concentration of these additives. Preferably, such concentrates will comprise from about 0.1 to about 20 weight percent of a cellulase composition described above (protein); from about 10 to about 50 weight percent buffer; from about 10 to about 50 weight percent surfactant; and from about 0 to about 80 weight percent water. When aqueous concentrates are formulated, these concentrates can be diluted by factors of from about 2 to about 200 so as to arrive at the requisite concentration of the components in the cellulase solution. As is readily apparent, such concentrates will permit facile formulation of the cellulase solutions as well as permit feasible transportation of the concentration to the location where it will be used. The cellulase composition as described above can be added to the concentrate either in a liquid diluent, in granules, in emulsions, in gels, in pastes, and the like. Such forms are well known to the skilled artisan.

When a solid cellulase concentrate is employed, the cellulase composition is generally a granule, a powder, an agglomeration, and the like. When granules are used, the granules can preferably be formulated so as to contain a cellulase protecting agent. See, for instance, U.S. Ser. No. 07/642,669, filed Jan. 17, 1991 and entitled "GRANULES CONTAINING BOTH AN ENZYME AND AN ENZYME PROTECTING AGENT AND DETERGENT COMPOSITIONS CONTAINING SUCH GRANULES" which application is incorporated herein by reference in its entirety. Likewise, the granules can be formulated so as to contain materials to reduce the rate of dissolution of the granules into the wash medium. Such materials and granules are Jan. 17, 1991 and entitled "GRANULAR COMPOSITIONS" which application is incorporated herein by reference in its entirety.

It is contemplated that the cellulase compositions described herein can additionally be used in a pre-wash and as a pre-soak either as a liquid or a spray. It is still further contemplated that the cellulase compositions described herein can also be used in home use as a stand alone composition suitable for enhancing color and appearance of fabrics. See, for example, U.S. Pat. No. 4,738,682, which is incorporated herein by reference in its entirety.

The following examples are offered to illustrate the present invention and should not be construed in any way as limiting its scope.

EXAMPLES

Examples 1-12 demonstrate the preparation of *Trichoderma longibrachiatum* genetically engineered so as to be incapable of producing one or more cellulase components or so as to overproduce specific cellulase components.

EXAMPLE 1

Selection for pyr4 mutants of *Trichoderma longibrachiatum*

The pyr4 gene encodes orotidine-5'-monophosphate decarboxylase, an enzyme required for the biosynthesis of uridine. The toxic inhibitor 5-fluoroorotic acid (FOA) is incorporated into uridine by wild-type cells and thus poisons the cells. However, cells defective in the pyr4 gene are resistant to this inhibitor but require uridine for growth. It is, therefore, possible to select for pyr4 mutant strains using FOA. In practice, spores of *Trichoderma longibrachiatum* strain RL-P37 (Sheir-Neiss G. and Montenecourt, B. S., 1984, Appl. Microbiol. Biotechnol. 20:46-53) were spread on the surface of a solidified medium containing 2 mg/ml uridine and 1.2 mg/ml FOA. Spontaneous FOA-resistant colonies appeared within three to four days and it was possible to subsequently identify those FOA-resistant mutants which required uridine for growth. In order to identify those mutants which specifically had a defective pyr4 gene, protoplasts were generated and transformed with a plasmid containing a wild-type pyr4 gene (see Examples 3 and 4). Following transformation, protoplasts were plated on medium lacking uridine. Subsequent growth of transformed colonies demonstrated complementation of a defective pyr4 gene by the plasmid-borne pyr4 gene. In this way strain GC69 was identified as a pyr4⁻ mutant of strain RL-P37.

EXAMPLE 2

Preparation of CBHI Deletion Vector

A cbh1 gene encoding the CBHI protein was cloned from the genomic DNA of strain RL-P37 by hybridization with an oligonucleotide probe designed on the basis of the published sequence for this gene using known probe synthesis methods (Shoemaker et al., "Molecular Cloning of Exo-cellobiohydrolase I Derived from *Trichoderma longibrachiatum* Strain L27", Bio/Technology 1, p. 691 (1983). The cbh1 gene resides on a 6.5 kb PstI fragment and was inserted into PstI cut pUC4K (purchased from Pharmacia Inc., Piscataway, N.J.) replacing the Kan, gene of this vector. The resulting plasmid, pUC4K::cbhI was then cut with HindIII and the larger fragment of about 6 kb was isolated and religated to give pUC4K::cbhIΔH/H. This procedure removes the entire cbh1 coding sequence and approximately 1.2 kb upstream and 1.5 kb downstream of flanking DNA from either side of the original PstI fragment.

The *Trichoderma longibrachiatum* pyr4 gene was cloned as a 6.5 kb fragment of genomic DNA in pUC18 following the methods of Sanbrook et al., 1989, "Molecular Cloning, A Laboratory Manuel", 2nd Ed., Cold Springs Harbor Laboratory Press. The plasmid pUC4K::cbhIΔH/H was cut with HindIII and the ends were desphosphorylated with calf intestinal alkaline phosphatase. This end dephosphorylated DNA was ligated with the 6.5 kb HindIII fragment containing the *Trichoderma longibrachiatum* pyr4 gene to give pΔCBHIpyr4. See FIG. 1.

EXAMPLE 3

Isolation of Protoplasts

Mycelium was obtained by inoculating 100 ml of YEG (0.5% yeast extract, 2% glucose) in a 500 ml flask with about $5 \times 10^7$ *Trichoderma longibrachiatum* GC69 spores (the pyr4⁻ mutant strain). The flask was then incubated at 37° C. with shaking for about 16 hours. The mycelium was harvested by centrifugation at 2,750×g. The harvested mycelium was further washed in 1.2M sorbitol solution and resuspended in 40 ml of Novozym ® 234 solution (which is the tradename for a multicomponent enzyme system containing 1,3-alpha-glucanase, 1,3-beta-glucanase, laminarinase, xylanase, chitinase and protease from Novo Biolabs, Danbury Conn.) containing 5 mg/ml Novozym ® 234; 5 mg/ml MgSO₄.7H₂O; 0.5 mg/ml bovine serum albumin; 1.2M sorbitol. The protoplasts were removed from cellular debris by filtration through Miracloth (Calbiochem Corp., LaJolla, Calif.) and collected by centrifugation at 2,000×g. The protoplasts were washed three times in 1.2M sorbitol and once in 1.2M sorbitol, 50 mM CaCl₂, centrifuged and resuspended. The protoplasts were finally resuspended at a density of $2 \times 10^8$ protoplasts per ml of 1.2M sorbitol, 50 mM CaCl₂.

EXAMPLE 4

Transformation of Fungal Protoplasts

200 μl of the protoplast suspension prepared in Example 3 was added to 20 μl of EcoRI digested pΔCBHIpyr4 (prepared in Example 2) in TE buffer (10 mM Tris, pH 7.4; 1 mM EDTA) and 50 μl of a polyethylene glycol (PEG) solution containing 25% PEG 4000, 0.6M KCl and 50 mM CaCl₂. This mixture was incubated on ice for 20 minutes. After this incubation period 2.0 ml of the above-identified PEG solution was added thereto, the solution was further mixed and incubated at room temperature for 5 minutes. After this second incubation, 4.0 ml of a solution containing 1.2M sorbitol and 50 mM CaCl₂ was added thereto and this solution was further mixed. The protoplast solution was then immediately added to molten aliquots of Vogel's Medium N (3 grams sodium citrate, 5 grams KH₂PO₄, 2 grams NH₄NO₃, 0.2 grams MgSO₄.7H₂O, 0.1 gram CaCl₂.2H₂O, 5 μg α-biotin, 5 mg citric acid, 5 mg ZnSO₄.7H₂O, 1 mg Fe(NH₄)₂.6H₂O, 0.25 mg CuSO₄.5H₂O, 50 μg MnSO₄.4H₂O per liter) containing an additional 1% glucose, 1.2M sorbitol and 1% agarose. The protoplast/medium mixture was then poured onto a solid medium containing the same Vogel's medium as stated above. No uridine was present in the medium and therefore only transformed colonies were able to grow as a result of complementation of the pyr4 mutation of strain GC69 by the wild type pyr4 gene present in pΔCBHIpyr4. These colonies were subsequently transferred and stable transformants purified, on a solid Vogel's medium N containing as an additive, 1% glucose.

EXAMPLE 5

Analysis of the Transformants

DNA was isolated from the transformants obtained in Example 4 after they were grown in the liquid Vogel's medium N containing 1% glucose. These transformant DNA samples were further cut with a PstI restriction enzyme and subjected to agarose gel electrophoresis. The gel was then further blotted onto a Nytran membrane filter and hybridized with a ³²P labelled pΔCBHIpyr4 probe. The probe was selected to identify the native cbh1 gene as a 6.5 kb PstI fragment, the native pyr4 gene and any DNA sequences derived from the transforming DNA fragment. FIG. 2 outlines deletion of the *Trichoderma longibrachiatum* cbh1 gene by integration of the larger EcoRI fragment from pΔCBHIpyr4 at the cbh1 locus on one of the *Trichoderma longibrachiatum*.

The bands from the hybridization were visualized via autoradiography. The result of the autoradiograph is seen in FIG. 3. Five samples were run as described above, hence samples A, B, C, D, and E. Lane E is the untransformed strain GC69 and was used as a control in the present analysis. Lanes A-D represent transformants obtained from the methods described above. The numbers on the side of the autoradiograph represent the sizes of molecular weight markers. As can be seen from this autoradiograph, Lane D does not contain the 6.5 kb CBH I band, indicating that this gene has been totally deleted in the transformant. This cbh1 deleted strain is called P37PΔCBHI. The other transformants analyzed appear identical to the untransformed control strain. Presumably, this happened because the linear fragment from pΔCBHIpyr4 integrated by a double cross-over at the native pyr4 locus to give a gene replacement event.

EXAMPLE 6

The same procedure was used in this example as in Example 5, except that the probe used was changed to a $^{32}$P labelled pIntCBHI probe. This probe is a pUC-type plasmid containing a 2 kb BglII fragment from the cbh1 locus within the region that was deleted in pUC4::cbh1ΔH/H. Two samples were run in this example including a control sample A, which is the untransformed strain GC69 and the transformant P37PΔCBHI, sample B. As can be seen in FIG. 4, sample A contained the cbh1 gene, as indicated by the band at 6.5 kb; however the transformant, sample B does not contain this 6.5 kb band and therefore does not contain the cbh1 gene.

EXAMPLE 7

Protein Secretion by Strain P37PΔCBHI

Spores from the produced P37PΔCBHI strain were inoculated into 50 ml of a Trichoderma basal medium containing 1% glucose, 0.14% $(NH_4)_2SO_4$, 0.2% $KH_2PO_4$, 0.03% $MgSO_4$, 0.03% urea, 0.75% bactotryptone, 0.05% Tween 80, 0.000016% $CuSO_4.5H_2O$, 0.001% $FeSO_4.7H_2O$, 0.000128% $ZnSO_4.7H_2O$, 0.0000054% $Na_2MoO_4.2H_2O$, 0.0000007% $MnCl.4H_2O$). The medium was incubated while shaking in a 250 ml flask at 37° C. for about 48 hours. The resulting mycelium was collected by filtering through Miracloth (Calbiochem Corp. LaJolla, Calif.) and washed two or three times with 17 mM potassium phosphate. The mycelium was finally suspended in 17 mM potassium phosphate with 1 mM sophorose and further incubated for 24 hours at 30° C. while shaking. The supernatant was then collected from these cultures and the mycelium was discarded. Samples of the culture supernatant were analyzed by isoelectric focusing using a Pharmacia Phastgel system and pH 3-9 precast gels according to the manufacturer's instructions. The gel was stained with silver stain to visualize the protein bands. The band corresponding to the cbh1 protein was absent from the sample derived from the strain P37PΔCBHI, as shown in FIG. 5. This isoelectric focusing gel shows various proteins in different supernatant cultures of *Trichoderma longibrachiatum*. Lane A is partially purified CBH I; Lane B is the supernatant from an untransformed *Trichoderma longibrachiatum* culture; Lane C is the supernatant from a strain deleted for the cbh1 gene produced according to the methods of the present invention. The position of various cellulase components are labelled. Since CBHI constitutes about 50% of the total extracellular protein, it is the major secreted protein and hence is the darkest band on the gel. This isoelectric focusing gel clearly shows depletion of the CBHI protein in the strain deleted for cbh1.

EXAMPLE 8

Preparation of pPΔCBHII

The cbh2 gene of *Trichoderma longibrachiatum*, encoding the CBH II protein, has been cloned as a 4.1 kb EcoRI fragment of genomic DNA which is shown diagrammatically in FIG. 6A (Chen et al., 1987, Biotechnology, 5:274-278). Using methods known in the art, a plasmid, pPΔCBHII (FIG. 6B), has been constructed in which a 1.7 kb central region of this clone between a HindIII site (at 74 bp 3' of the CBHII translation initiation site) and a ClaI site (at 265 bp 3' of the last codon of CBHII) has been removed and replaced by the *Trichoderma longibrachiatum* pyr4 gene.

Digestion of this plasmid with EcoRI will liberate a fragment having 0.7 kb of flanking DNA from the cbh2 locus at one end, 1.7 kb of flanking DNA from the cbh2 locus at the other end and the *Trichoderma longibrachiatum* pyr4 gene in the middle.

EXAMPLE 9

Generation of a pyr4$^-$ mutant of P37PΔCBHI

Spores of the transformant (P37PΔCBHI) which was deleted for the cbh1 gene were spread onto medium containing FOA. A pyr4$^-$ derivative of this transformant was subsequently obtained using the methods of Example 1. This pyr4$^-$ strain was designated P37PΔCBHIPyr$^-$26.

EXAMPLE 10

Deletion of cbh2 gene in a strain previously deleted for cbh1

Protoplasts of strain P37PΔCBHIPyr$^-$26 were generated and transformed with EcoRI digested pPΔCBHII according to the methods outlined in Examples 3 and 4.

Purified stable transformants were cultured in shake flasks as in Example 7 and the protein in the culture supernatants was examined by isoelectric focusing. One transformant (designated P37PΔΔCBH67) was identified which did not produce any CBH II protein. Lane D of FIG. 5 shows the supernatant from a strain deleted for both the cbh1 and cbh2 genes produced according to the methods of the present invention.

DNA was extracted from strain P37PΔΔCBH67, digested with EcoRI and Asp718, and subjected to agarose gel electrophoresis. The DNA from this gel was blotted to a membrane filter and hybridized with $^{32}$P labelled pPΔCBHII (FIG. 7). Lane A of FIG. 7 shows the hybridization pattern observed for DNA from an untransformed *Trichoderma longibrachiatum* strain. The 4.1 kb EcoRI fragment containing the wild-type cbh2 gene was observed. Lane B shows the hybridization pattern observed for strain P37PΔΔCBH67. The single 4.1 kb band has been eliminated and replaced by two bands of approximately 0.9 and 3.1 kb. This is the expected pattern if a single copy of the EcoRI fragment from pPΔCBHII had integrated precisely at the cbh2 locus.

The same DNA samples were also digested with EcoRI and Southern analysis was performed as above.

In this example, the probe was $^{32}$P labelled pIntCBHII. This plasmid contains a portion of the cbh2 gene coding sequence from within that segment of cbh2 DNA which was deleted in plasmid pPΔCBHII. No hybridization was seen with DNA from strain P37PΔΔCBH67 showing that the cbh2 gene was deleted and that no sequences derived from the pUC plasmid were present in this strain.

EXAMPLE 11

Construction of pEGIpyr4

The *Trichoderma longibrachiatum* egl1 gene, which encodes EGI, has been cloned as a 4.2 kb HindIII fragment of genomic DNA from strain RL-P37 by hybridization with oligonucleotides synthesized according to the published sequence (Penttila et al., 1986, Gene 45 253-263). A 3.6 kb HindIII-BamHI fragment was taken from this clone and ligated with a 1.6 kb HindIII-BamHI fragment containing the *Trichoderma longibrachiatum* pyr4 gene and a pUC-based plasmid cut with HindIII to give the plasmid pEGIpyr4 (FIG. 8). Digestion of pEGIpyr4 with HindIII would liberate a fragment of DNA containing only *Trichoderma longibrachiatum* genomic DNA (the egl1 and pyr4 genes) except for 24 bp of sequenced, synthetic DNA between the two genes and 6 bp of sequenced, synthetic DNA at one end (see FIG. 8).

EXAMPLE 12

Transformants of *Trichoderma longibrachiatum* containing pEGIpyr4

A pyr4 defective mutant of *Trichoderma longibrachiatum* strain RutC30 (Sheir-Neiss and Montenecourt, 1984, Appl. Microbiol. Biotechnol. 20:46-53) was obtained by the method outlined in Example 1. Protoplasts of this strain were transformed with undigested pEGIpyr4 and stable transformants were purified. Five of these transformants (designated EP2, EP4, EP5, EP6, EP11), as well as untransformed RutC30 were inoculated into 50 ml of YEG medium (yeast extract, 5 g/l; glucose, 20 g/l) in 250 ml shake flasks and cultured with shaking for 2 days at 28° C. The resulting mycelium was washed with sterile water and added to 50 ml of TSF medium (0.05M citrate-phosphate buffer, pH 5.0; Avicel microcrystalline cellulose, 10 g/l; KH$_2$PO$_4$, 2.0 g/l; (NH$_4$)$_2$SO$_4$, 1.4 g/l; proteose peptone, 1.0 g/l; Urea, 0.3 g/l; MgSO$_4$.7H$_2$O, 0.3 g/l; CaCl$_2$, 0.3 g/l; FeSO$_4$.7H$_2$O, 5.0 mg/l; MnSO$_4$.H$_2$O, 1.6 mg/l; ZnSO$_4$, 1.4 mg/l; CoCl$_2$, 2.0 mg/l; 0.1% Tween 80). These cultures were incubated with shaking for a further 4 days at 28° C. Samples of the supernatant were taken from these cultures and assays designed to measure the total amount of protein and of endoglucanase activity were performed as described below.

The endoglucanase assay relied on the release of soluble, dyed oligosaccharides from Remazol Brilliant Blue - carboxymethylcellulose (RBB-CMC, obtained from MegaZyme, North Rocks, NSW, Australia). The substrate was prepared by adding 2 g of dry RBB-CMC to 80 ml of just boiled deionized water with vigorous stirring. When cooled to room temperature, 5 ml of 2M sodium acetate buffer (pH 4.8) was added and the pH adjusted to 4.5. The volume was finally adjusted to 100 ml with deionized water and sodium azide added to a final concentration of 0.02%. Aliquots of *Trichoderma longibrachiatum* culture supernatant or 0.1M sodium acetate as a blank (10-20 μl) were placed in tubes, 250 μl of substrate was added and the tubes were incubated for 30 minutes at 37° C. The tubes were placed on ice for 10 minutes and 1 ml of cold precipitant (3.3% sodium acetate, 0.4% zinc acetate, pH 5 with HCl, 76% ethanol) was then added. The tubes were vortexed and allowed to sit for 5 minutes before centrifuging for 3 minutes at approximately 13,000 xg. The optical density was measured spectrophotometrically at a wavelength of 590-600 nm.

The protein assay used was the BCA (bicinchoninic acid) assay using reagents obtained from Pierce, Rockford, Ill., USA. The standard was bovine serum albumin (BSA). BCA reagent was made by mixing 1 part of reagent B with 50 parts of reagent A. One ml of the BCA reagent was mixed with 50 μl of appropriately diluted BSA or *Trichoderma longibrachiatum* culture supernatant. Incubation was for 30 minutes at 37° C. and the optical density was finally measured spectrophotometrically at a wavelength of 562 nm.

The results of the assays described above are shown in Table 1. It is clear that some of the transformants produced increased amounts of endoglucanase activity compared to untransformed strain RutC30. It is thought that the endoglucanases or exo-cellobiohydrolases produced by untransformed *Trichoderma longibrachiatum* constitute approximately 20% and 70% respectively of the total amount of protein secreted. Therefore a transformant such as EP5, which produces approximately four-fold more endoglucanase than strain RutC30, would be expected to secrete approximately equal amounts of endoglucanase type and exo-cellobiohydrolase type proteins.

The transformants described in this example were obtained using intact pEGIpyr4 and will contain DNA sequences integrated in the genome which were derived from the pUC plasmid. Prior to transformation it would be possible to digest pEGIpyr4 with HindIII and isolate the larger DNA fragment containing only *Trichoderma longibrachiatum* DNA. Transformation of *Trichoderma longibrachiatum* with this isolated fragment of DNA would allow isolation of transformants which overproduced EGI and contained no heterologous DNA sequences except for the two short pieces of synthetic DNA shown in FIG. 8. It would also be possible to use pEGIpyr4 to transform a strain which was deleted for either the cbh1 gene, or the cbh2 gene, or for both genes. In this way a strain could be constructed which would over-produce EGI and produce either a limited range of, or no, exo-cellobiohydrolases.

The methods of Example 12 could be used to produce *Trichoderma longibrachiatum* strains which would over-produce any of the other endoglucanases normally produced by (*Trichoderma longibrachiatum*).

TABLE 1

| STRAIN | A ENDOGLUCANASE ACTIVITY (O.D. AT 590 nm) | B PROTEIN (mg/ml) | A/B |
|---|---|---|---|
| RutC30 | 0.32 | 4.1 | 0.078 |
| EP2 | 0.70 | 3.7 | 0.189 |
| EP4 | 0.76 | 3.65 | 0.208 |
| EP5 | 1.24 | 4.1 | 0.302 |
| EP6 | 0.52 | 2.93 | 0.177 |
| EP11 | 0.99 | 4.11 | 0.241 |

The above results are presented for the purpose of demonstrating the overproduction of the EGI component and not for the purpose of the extent of overproduction. In this regard, the extent of overproduction is expected to vary with each experiment.

Example 13 demonstrates the isolation of the components of CYTOLASE 123 Cellulase (a complete fungal cellulase composition obtained from *Trichoderma longibrachiatum* and available from Genencor International, Inc., South San Francisco, Calif.) via purification procedures.

EXAMPLE 13

Purification of CYTOLASE 123 Cellulase into Cellulase Components

CYTOLASE 123 cellulase was fractionated in the following manner. The normal distribution of cellulase components in this cellulase system is as follows:

| CBH I | 45-55 weight percent |
|-------|----------------------|
| CBH II | 13-15 weight percent |
| EG I | 11-13 weight percent |
| EG II | 8-10 weight percent |
| EG III | 1-4 weight percent |
| BG | 0.5-1 weight percent. |

The fractionation was done using columns containing the following resins: Sephadex G-25 gel filtration resin from Sigma Chemical Company (St. Louis, Mo.), QA Trisacryl M anion exchange resin and SP Trisacryl M cation exchange resin from IBF Biotechnics (Savage, Md.). CYTOLASE 123 cellulase, 0.5g, was desalted using a column of 3 liters of Sephadex G-25 gel filtration resin with 10 mM sodium phosphate buffer at pH 6.8. The desalted solution, was then loaded onto a column of 20 ml of QA Trisacryl M anion exchange resin. The fraction bound on this column contained CBH I and EG I. These components were separated by gradient elution using an aqueous gradient containing from 0 to about 500 mM sodium chloride. The fraction not bound on this column contained CBH II and EG II. These fractions were desalted using a column of Sephadex G-25 gel filtration resin equilibrated with 10 mM sodium citrate, pH 3.3. This solution, 200 ml, was then loaded onto a column of 20 ml of SP Trisacryl M cation exchange resin. CBH II and EG II were eluted separately using an aqueous gradient containing from to about 200 mM sodium chloride.

Following procedures similar to that of Example 13 above, other cellulase systems which can be separated into their components include CELLUCAST (available from Novo Industry, Copenhagen, Denmark), RAPIDASE (available from Gist Brocades, N.V., Delft, Holland), and cellulase systems derived from *Trichoderma koningii, Penicillum sp.* and the like.

EXAMPLE 14

Purification of EG III from CYTOLASE 123 Cellulase

Example 13 above demonstrated the isolation of several components from CYTOLASE 123 Cellulase. However, because EG III is present in very small quantities in CYTOLASE 123 Cellulase, the following procedures were employed to isolate this component.

A. Large Scale Extraction of EG III Cellulase Enzyme

One hundred liters of cell free cellulase filtrate were heated to about 30° C. The heated material was made about 4% wt/vol PEG 8000 (polyethylene glycol, MW of about 8000) and about 10% wt/vol anhydrous sodium sulfate. The mixture formed a two phase liquid mixture. The phases were separated using an SA-1 disk stack centrifuge. The phases were analyzed using silver staining isoelectric focusing gels. Separation was obtained for EG III and xylanase. The recovered composition contained about 20 to 50 weight percent of EG III.

Regarding the above procedure, use of a polyethylene glycol having a molecular weight of less than about 8000 gave inadequate separation; whereas, use of polyethylene glycol having a molecular weight of greater than about 8000 resulted in the exclusion of desired enzymes in the recovered composition. With regard to the amount of sodium sulfate, sodium sulfate levels greater than about 0% wt/vol caused precipitation problems; whereas, sodium sulfate levels less than about 10% wt/vol gave poor separation or the solution remained in a single phase.

B. Purification of EG III Via Fractionation

The purification of EG III is conducted by fractionation from a complete fungal cellulase composition (CYTOLASE 123 cellulase, commercially available from Genencor International, South San Francisco, Calif.; which is produced by wild type *Trichoderma longibrachiatum*. Specifically, the fractionation is done using columns containing the following resins: Sephadex G-25 gel filtration resin from Sigma Chemical Company (St. Louis, Mo.), QA Trisacryl M anion exchange resin and SP Trisacryl M cation exchange resin from IBF Biotechnics (Savage, Md.). CYTOLASE 123 cellulase, 0.5 g, is desalted using a column of 3 liters of Sephadex G-25 gel filtration resin with 10 mM sodium phosphate buffer at pH 6.8. The desalted solution, is then loaded onto a column of 20 ml of QA Trisacryl M anion exchange resin. The fraction bound on this column contained CBH I and EG I. The fraction not bound on this column contains CBH II, EG II and EG III. These fractions are desalted using a column of Sephadex G-25 gel filtration resin equilibrated with 10 mM sodium citrate, pH 4.5. This solution, 200 ml, is then loaded onto a column of 20 ml of SP Trisacryl M cation exchange resin. The EG III was eluted with 100 mL of an aqueous solution of 200 mM sodium chloride.

In order to enhance the efficiency of the isolation of EG III, it may be desirable to employ *Trichoderma longibrachiatum* genetically modified so as to be incapable of producing one or more of EG I, EG II, CBH I and/or CBH II. The absence of one or more of such components will necessarily lead to more efficient isolation of EG III.

Likewise, it may be desirable for the EG III compositions described above to be further purified to provide for substantially pure EG III compositions, i.e., compositions containing EG III at greater than about 80 weight percent of protein. For example, such a substantially pure EG III protein can be obtained by utilizing material obtained from procedure A in procedure B or vica versa. One particular method for further purifying EG III is by further fractionation of an EG III sample obtained in part b) of this Example 14. The further fraction was done on a FPLC system using a Mono-S-HR 5/5 column (available from Pharmacia LKB Biotechnology, Piscataway, N.J.). The FPLC system consists of a liquid chromatography controller, 2 pumps, a dual path monitor, a fraction collector and a chart recorder (all of which are available from Pharmacia LKB Biotechnology, Piscataway, N.J.). The fractionation was conducted by desalting 5 ml of the EG III sample prepared in part b) of this Example 14 with a 20 ml Sephadex G-25 column which had been previously equilibrated with 10 mM sodium citrate pH 4. The column was then eluted with 0-200 mM aqueous gradient of NaCl at a rate of 0.5 ml/minute with samples collected in 1 ml fractions. EG III was recovered in fractions 10 and 11 and was determined to be greater than 90% pure by SDS gel electrophoresis. EG III of this purity is suitable for determining the N-terminal amino acid sequence by known techniques.

Substantially pure EG III as well as EG I and EG II components purified in Example 13 above can be used singularly or in mixtures in the methods of this invention. These EG components have the following characteristics:

|        | MW        | pI  | pH optimum[1] |
|--------|-----------|-----|---------------|
| EG I   | ~47-49 kD | 4.7 | ~5            |
| EG II  | ~35 kD    | 5.5 | ~5            |
| EG III | ~25-28 kD | 7.4 | ~5.5-6.0      |

[1]pH optimum determined by RBB-CMC activity as per Example 15 below.

The use of a mixture of these components in the practice of this invention may give a synergistic response in improving softening, feel, appearance, etc., as compared to a single component. On the other hand, the use of a single component in the practice of this invention may be more stable or have a broader spectrum of activity over a range of pHs. For instance, Example 15 below shows that EG III has considerable activity against RBB-CMC under alkaline conditions.

EXAMPLE 15

Activity of Cellulase Compositions Over a pH Range

The following procedure was employed to determine the pH profiles of two different cellulase compositions. The first cellulase composition was a CBH I and II deleted cellulase composition prepared from *Trichoderma longibrachiatum* genetically modified in a manner similar to that described above so as to be unable to produce CBH I and CBH II components. Insofar as this cellulase composition does not contain CBH I and CBH II which generally comprise from about 58 to 70 percent of a cellulase composition derived from *Trichoderma longibrachiatum*, this cellulase composition is necessarily substantially free of CBH I type and CBH II type cellulase components and accordingly, is enriched in EG components, i.e., EG I, EG II, EG III and the like.

The second cellulase composition was an approximately 20 to 40% pure fraction of EG III isolated from a cellulase composition derived from *Trichoderma longibrachiatum* via purification methods similar to part b) of Example 14.

The activity of these cellulase compositions was determined at 40° C. and the determinations were made using the following procedures.

Add 5 to 20 μl of an appropriate enzyme solution at a concentration sufficient to provide the requisite amount of enzyme in the final solution. Add 250 μl of 2 weight percent RBB-CMC (Remazol Brilliant Blue R-Carboxymethylcellulose—commercially available from MegaZyme, 6 Altona Place, North Rocks, N.S.W. 2151, Australia) in 0.05M citrate/phosphate buffer at pH 4, 5, 5.5, 6, 6.5, 7, 7.5 and 8.

Vortex and incubate at 40° C. for 30 minutes. Chill in an ice bath for 5 to 10 minutes. Add 1000 μl of methyl cellosolve containing 0.3M sodium acetate and 0.02M zinc acetate. Vortex and let sit for 5-10 minutes. Centrifuge and pour supernatant into cuvets. Measure the optical density (OD) of the solution in each cuvet at 590 nm. Higher levels of optical density correspond to higher levels of enzyme activity.

The results of this analysis are set forth in FIG. 9 which illustrates the relative activity of the CBH I and II deleted cellulase composition compared to the EG III cellulase composition. From this figure, it is seen that the cellulase composition deleted in CBH I and CBH II possesses optimum cellulolytic activity against RBB-CMC at near pH 5.5 and has some activity at alkaline pHs, i.e., at pHs from above 7 to 8. On the other hand, the cellulase composition enriched in EG III possesses optimum cellulolytic activity at pH 5.5-6 and possesses significant activity at alkaline pHs.

From the above example, one skilled in the art would merely need to adjust and maintain the pH of the aqueous textile composition so that the cellulase composition is active and preferably, possesses optimum activity. As noted above, such adjustments and maintenance may involve the use of a suitable buffer.

EXAMPLE 16

Launderometer Strength Loss Assay Cellulase Compositions

This example examines the ability of different cellulase compositions to reduce the strength of cotton-containing fabrics. This example employs an aqueous cellulase solution maintained at pH 5 because the activity of most of the cellulase components derived from *Trichoderma longibrachiatum* is greatest at or near pH 5 and accordingly, strength loss results will be most evident when the assay is conducted at about this pH.

Specifically, in this example, the first cellulase composition analyzed was a complete fungal cellulase system (CYTOLASE 123 cellulase, commercially available from Genencor International, South San Francisco, Calif.) produced by wild type *Trichoderma longibrachiatum* and is identified as GC010.

The second cellulase composition analyzed was a CBH II deleted cellulase composition prepared from *Trichoderma longibrachiatum* genetically modified in a manner similar to Examples 1 to 12 above so as to be incapable of expressing CBH II and is identified as CBHIId. Insofar as CBH II comprises up to about 15 percent of the cellulase composition, deletion of this component results in enriched levels of CBH I, and all of the EG components.

The third cellulase composition analyzed was a CBH I and CBH II deleted cellulase composition prepared from *Trichoderma longibrachiatum* genetically modified in a manner similar to that described above so as to be incapable of expressing CBH I and CBH II and is identified as CBHI/IId. Insofar as CBH I and CBH II are not produced by this modified microorganism, the cellulase is necessarily free of all CBH I type components as well as all CBH components.

The last cellulase composition analyzed was a CBH I deleted cellulase composition prepared from *Trichoderma longibrachiatum* genetically modified in a manner similar to that described above so as to be incapable of expressing CBH I and is identified as CBHId. Insofar as the modified microorganism is incapable of expressing CBH I, this cellulase composition is necessarily free of all CBH I type cellulase components.

The cellulase compositions described above were tested for their effect on cotton-containing fabric strength loss in a launderometer. The compositions were first normalized so that equal amounts of EG components were used. Each cellulase composition was then added to separate solutions of 400 ml of a 20 mM citrate/phosphate buffer, titrated to pH 5, and which contains 0.5 ml of a non-ionic surfactant. Each of the resulting solutions was then added to a separate launderometer canister. Into these canisters were added a quantity of marbles to facilitate strength loss as well as a 16 inch×20 inch cotton fabric (100% woven cotton, available as Style No. 467 from Test Fabrics, Inc., 200 Blackford Ave., Middlesex, N.J. 08846). The canister was then closed and the canister lowered into the launderometer bath which was maintained at 43° C. The canister was then rotated in the bath at a speed of at least about 40 revolutions per minute (rpms) for about 1 hour. Afterwards, the cloth is removed, rinsed well and dried in a standard drier.

In order to maximize strength loss results, the above procedure was repeated twice more and after the third treatment, the cotton fabrics were removed and analyzed for strength loss. Strength loss was measured by determining the tensile strength in the fill direction ("FTS") using a Instron Tester and the results compared to the FTS of the fabric treated with the same solution with the exception that no cellulase was added. The results of this analysis are reported as percent strength loss which is determined as follows:

$$\% \text{ Strength Loss} = 100 \times \left[ 1 - \frac{FTS \text{ with cellulase}}{FTS \text{ without cellulase}} \right]$$

The results of this analysis are set forth in FIG. 10 which shows that compositions containing CBH I, i.e., whole cellulase (GC010) and CBH II deleted cellulase, possessed the most strength loss whereas, the compositions containing no CBH I possessed significantly reduced strength loss as compared to whole cellulase and CBH II deleted cellulase. From these results, it is seen that the presence of CBH I type components in a cellulase composition imparts increased strength loss to the composition as compared to a similar composition not containing CBH I type components.

Likewise, these results show that CBH II plays some role in strength loss.

Accordingly, in view of these results, strength loss resistant cellulase compositions are those compositions free of all CBH I type cellulase components and preferably, all CBH type cellulase components. In this regard, it is contemplated that such cellulase compositions will result in even lower strength loss at pH≧7 than those results observed at pH 5 shown in FIG. 10.

During the manufacture of cotton-containing fabrics, the fabric can become stressed and when so stressed, it will contain broken and disordered fibers. Such fibers detrimentally impart a worn and dull appearance to the fabric. However, it has been found that the methods of this invention will result in fabric/color enhancement. This is believed to arise by removal of some of the broken and disordered fibers which has the effect of restoring the appearance of the fabric prior to becoming stressed.

The following Examples 17 and 18 illustrate this benefit of the present invention. It is noted that these example employed worn cotton T-shirts (knits) as well as new cotton knits. The faded appearance of the worn cotton-containing fabric arises from the accumulation on the fabric of broken and loose surface fibers over a period of time. These fibers give rise to a faded and matted appearance for the fabric and accordingly, the removal of these fibers is a necessary prerequisite to restoring the original sharp color to the fabric. Additionally, the accumulation of broken surface fibers on new cotton knits imparts a dull appearance to such fabrics. Accordingly, these experiments are necessarily applicable to color enhancement of stressed cotton-containing fabrics because both involve removal of surface fibers from the fabric.

EXAMPLE 17

Color Enhancement

The ability of EG components to enhance color in cotton-containing fabrics was analyzed in the following experiments. Specifically, the first experiment measures the ability of a complete cellulase system (CYTOLASE 123 cellulase, commercially available from Genencor International, South San Francisco, Calif.) produced by wild type *Trichoderma longibrachiatum* to remove surface fibers from a cotton-containing fabric over various pHs. This cellulase was tested for its ability to remove surface fibers in a launderometer. An appropriate amount of cellulase to provide for either 25 ppm or 100 ppm cellulase in the final composition was added to separate solutions of 400 ml of a 20 mM citrate/phosphate buffer containing 0.5 ml of a non-ionic surfactant. Samples were prepared and titrated so as to provide for samples at pH 5, pH 6, pH 7 and pH 7.5. Each of the resulting solutions was then added to a separate launderometer canister. Into these canisters were added a quantity of marbles to facilitate fiber removal as well as a 7 inch×5 inch cotton fabric (100% woven cotton, available as Style No. 439W from Test Fabrics, Inc., 200 Blackford Ave., Middlesex, N.J. 08846). The canister was then closed and the canister lowered into the launderometer bath which was maintained at 43° C. The canister was then rotated in the bath at a speed of at least about 40 revolutions per minute (rpms) for about 1 hour. Afterwards, the cloth is removed, rinsed well and dried in a standard drier.

The so treated fabrics were then analyzed for fiber removal by evaluation in a panel test. In particular, the fabrics (unmarked) were rated for levels of fiber by 6 individuals. The fabrics were visually evaluated for surface fibers and rated on a 0 to 6 scale. The scale has six standards to allow meaningful comparisons. The standards are:

| Rating | Standard[a] |
| --- | --- |
| 0 | Fabric not treated with cellulase |
| 1 | Fabric treated[b] with 8 ppm cellulase |
| 2 | Fabric treated with 16 ppm cellulase |
| 3 | Fabric treated with 20 ppm cellulase |
| 4 | Fabric treated with 40 ppm cellulase |
| 5 | Fabric treated with 50 ppm cellulase |
| 6 | Fabric treated with 100 ppm cellulase |

[a]In all of the standards, the fabric was a 100% cotton sheeting standardized test fabric (Style No. 439W) available from Test Fabrics, Inc., 200 Blackford Ave., Middlesex, NJ 08846

[b]All samples were treated with the same cellulase composition. Cellulase concentrations are in total protein. The launderometer treatment conditions are the same as set forth in Example 16 above.

The fabric to be rated was provided a rating which most closely matched one of the standards. After complete analysis of the fabrics, the values assigned to each fabric by all of the individuals were added and an average value generated.

The results of this analysis are set forth in FIG. 11. Specifically, FIG. 11 illustrates that at the same pH, a dose dependent response is seen in the amount of fibers removed. That is to say that at the same pH, the fabrics treated with more cellulase provided for higher levels of fiber removal as compared to fabrics treated with less cellulase. Moreover, the results of this figure demonstrate that at higher pHs, fiber removal can still be effected merely by using higher concentrations of cellulase.

In a second experiment, two different cellulase compositions were compared for the ability to remove fiber. Specifically, the first cellulase composition analyzed was a complete cellulase system (CYTOLASE 123 cellulase, commercially available from Genencor International, South San Francisco, Calif.) produced by wild type *Trichoderma longibrachiatum* and is identified as GC010.

The second cellulase composition analyzed was a cellulase composition substantially free of all CBH type components (including CBH I type components) which composition was prepared from *Trichoderma longibrachiatum* genetically modified in a manner similar to that described above so as to be incapable of expressing CBH I and CBH II and is identified as CBHI/II deleted. Insofar as CBH I and CBH II comprises up to about 70 percent of the cellulase composition, deletion of this component results in enriched levels of all of the EG components.

These compositions were tested for their ability to remove surface fibers in a launderometer. An appropriate amount of cellulase to provide for the requisite concentrations of EG components in the final compositions were added to separate solutions of 400 ml of a 20 mM citrate/phosphate buffer containing 0.5 ml of a nonionic surfactant. Samples were prepared and titrated to pH 5. Each of the resulting solutions was then added to a separate launderometer canister. Into these canisters were added a quantity of marbles to facilitate fiber removal as well as a 7 inch×5 inch cotton fabric (100% woven cotton, available as Style No. 439W from Test Fabrics, Inc., 200 Blackford Ave., Middlesex, N.J. 08846). The canister was then closed and the canister lowered into the launderometer bath which was maintained at 43° C. The canister was then rotated in the bath at a speed of at least about 40 revolutions per minute (rpms) for about 1 hour. Afterwards, the cloth is removed, rinsed well and dried in a standard drier.

The so treated fabrics were then analyzed for fiber removal by evaluation in the panel test described above. The results of this analysis are set forth in FIG. 12 which is plotted based on estimated EG concentrations. Specifically, FIG. 12 illustrates that both GC010 and CBH I/II deleted cellulase compositions gave substantially identical fiber removal results at substantially equal EG concentrations. The results of this figure suggest that it is the EG components which provide for fiber removal. These results coupled with the results of FIG. 11 demonstrate that EG components remove surface fibers.

EXAMPLE 18

Tergotometer Color Enhancement

This example is further to Example 17 and substantiates that CBH type components are not necessary for color enhancement and the purpose of this example is to examine the ability of cellulase compositions deficient in CBH type components to enhance color to cotton-containing fabrics.

Specifically, the cellulase composition employed in this example was substantially free of all CBH type components (including CBH I type components) insofar as this composition was prepared from *Trichoderma longibrachiatum* genetically modified in a manner similar to that described above so as to be incapable of expressing CBH I and CBH II. Insofar as CBH I and CBH II comprises up to about 70 percent of the cellulase composition, deletion of this component results in enriched levels of all of the EG components.

The assay was conducted by adding a sufficient concentration of this cellulase composition to a 50 mM citrate/phosphate buffer to provide 500 ppm of cellulase. The solution was titrated to pH 5 and contained 0.1 weight percent of nonionic surfactant (Grescoterg GL100—commercially available from Gresco Mfg., Thomasville, N.C. 27360) A 10 inch×10 inch faded cotton-containing fabric as well as a 10 inch×10 inch new knitted fabric having loose and broken surface fibers were then placed into 1 liter of this buffer and allowed to sit at 110° F. for 30 minutes and then agitated for 30 minutes at 100 rotations per minute. The fabrics were then removed from the buffer, washed and dried. The resulting fabrics were then compared to the fabric prior to treatment. The results of this analysis are as follows:

| Cotton-Containing Material | Result |
| --- | --- |
| Worn Cotton T-Shirt | benefit seen |
| New Cotton Knit | benefit seen |

The term "benefit seen" means that the treated fabric exhibits color restoration (i.e., is less faded) as compared to the non-treated fabric which includes removal of broken surface fibers including broken surface fibers generated as a result of using the tergotometer. These results substantiate the results of Example 17 that the presence of CBH type components is not necessary for effecting color restoration of faded cotton-containing fabrics.

It is contemplated that the use of such cellulase compositions would be beneficial during fabric processing because such compositions would remove broken/loose fibers generated during processing without detrimental strength loss to the fabric.

EXAMPLE 19

Softness

This example demonstrates that the presence of CBH type components are not essential for imparting improved softness to cotton-containing fabrics. Specifically, this example employs a cellulase composition free of all CBH type components which composition is derived from *Trichoderma longibrachiatum* genetically engineered in the manner described above so as to be incapable of producing CBH I and II components.

This cellulase composition was tested for its ability to soften terry wash cloth. Specifically, unsoftened 8.5 ounce cotton terry cloths, 14 inches by 15 inches (available as Style No. 420NS from Test Fabrics, Inc., 200 Blackford Ave., Middlesex, N.J. 08846), were cut into 7 inch by 7.5 inch swatches.

The cellulase composition described above was tested for its ability to soften these swatches in a launderometer. Specifically, an appropriate amount of cellulase to provide for 500 ppm, 250 ppm, 100 ppm, 50 ppm, and 10 ppm cellulase in the final cellulase solution was added to separate solutions of 400 ml of a 20 mM citrate/phosphate buffer containing 0.025 weight percent of a non-ionic surfactant (Triton X114). Additionally, a blank was run containing the same solution but with no added cellulase. Samples so prepared were titrated to pH 5. Each of the resulting solution was then added to a separate launderometer canister. Into these canisters were added a quantity of marbles to facilitate softness as well as cotton swatches described above. All conditions were run in triplicate with two swatches per canister. Each canister was then closed and the canister lowered into the launderometer bath which was maintained at 37° C. The canister was then rotated in the bath at a speed of at least about 40 revolutions per minute (rpms) for about 1 hour. Afterwards, the swatches were removed, rinsed well and dried in a standard drier.

The swatches were then analyzed for softness by evaluation in a preference test. Specifically, six panelists were given their own set of swatches and asked to rate them with respect to softness based on the softness criteria such as the pliability of the whole fabric. Swatches obtained from treatment with the five different enzyme concentrations and the blank were placed behind a screen and the panelists were asked to order them from least soft to most soft. Scores were assigned to each swatch based on its order relative to the other swatches; 5 being most soft and 0 being least soft. The scores from each panelists were cumulated and then averaged.

The results of this averaging are set forth in FIG. 13. Specifically, these results demonstrate that at higher concentrations, improved softening is obtained. It is noted that this improved softening is achieved without the presence of either CBH I or II in the cellulase composition.

EXAMPLE 20

Feel and Appearance

This example demonstrates that the presence of CBH type components are not essential for imparting improved feel and appearance to cotton-containing fabrics. Specifically, this example employs a cellulase composition derived from *Trichoderma longibrachiatum* genetically engineered in the manner described above so as to be incapable of producing any CBH type components (i.e., incapable of producing CBH I and II components).

This cellulase composition was tested for its ability to improve the appearance of cotton-containing fabrics. Specifically, appropriately sized 100% cotton sheeting (available as Style No. 439W from Test Fabrics, Inc., 200 Blackford Ave., Middlesex, N.J. 08846) were employed in the appearance aspects of this example.

The cellulase composition described above was tested for its ability to improve the appearance of these samples in a launderometer. Specifically, an appropriate amount of CBH I and II deleted cellulase to provide for 25 ppm, 50 ppm, and 100 ppm cellulase in the final cellulase solution was added to separate solutions of 400 ml of a 20 mM citrate/phosphate buffer containing 0.025 weight percent of a non-ionic surfactant (Triton X114). Additionally, a blank was run containing the same solution but with no added cellulase. Samples so prepared were titrated to pH 5. Each of the resulting solutions was then added to a separate launderometer canister. Into these canisters were added a quantity of marbles to facilitate improvements in appearance as well as cotton samples described above. Each canister was then closed and the canister lowered into the launderometer bath which was maintained at about 40° C. The canister was then rotated in the bath at a speed of at least about 40 revolutions per minute (rpms) for about 1 hour. Afterwards, the samples were removed, rinsed well and dried in a standard drier.

The samples were then analyzed for improved appearance by evaluation in a preference test. Specifically, 6 panelists were given the 4 samples (not identified) and asked to rate them with respect to appearance. The panelists were instructed that the term "appearance" refers to the physical appearance of the cotton-containing fabric to the eye and is determined in part, by the presence or absence of, fuzz, surface fibers, and the like on the surface of the fabric as well as by the ability or inability to discern the construction (weave) of the fabric. Fabrics which have little if any fuzz and surface fibers and wherein the construction (weave) is clearly discernable possess improved appearance as compared to fabrics having fuzz and/or loose fibers and/or an indiscernible weave.

The panelists then assigned scores were assigned to each sample based on its order relative to the other samples; 4 having the best appearance and 1 having the worst appearance. The scores from each panelists were cumulated and then averaged. The results of this test are as follows:

| Amt Cellulase | Average Appearance |
| --- | --- |
| None | 1 |
| 25 ppm | 2 |
| 50 ppm | 3 |
| 100 ppm | 4 |

The CBH I and II deleted cellulase composition was then tested for its ability to improve the feel of cotton-containing fabrics. Specifically, appropriately sized 100% cotton sheeting (available as Style No. 439W from Test Fabrics, Inc., 200 Blackford Ave., Middlesex, N.J. 08846) were employed in the feel aspects of this example.

The cellulase composition described above was tested for its ability to improve the feel of these samples in a launderometer. Specifically, an appropriate amount of cellulase to provide for 500 ppm, 1000 ppm, and 2000 ppm cellulase in the final cellulase solution was added to separate solutions of 24 L of a 20 mM citrate/phosphate buffer. Additionally, a blank was run containing the same solution but with no added cellulase. All tests were conducted at pH 5.8 and run in an industial washer. The washer was operated at 50° C., a total volume of 24 L, a liquor to cloth ratio of 50:1 (weight to weight) and the washer was run for 30 minutes. Afterwards, the samples were removed and dried in an industrial dryer.

The samples were then analyzed for improved feel by evaluation in a preference test. Specifically, 5 panelists were given the 4 samples (not identified) and asked to rate them with respect to feel. The panelists were instructed that fabrics having improved feel are smoother and silkier to the touch than other fabrics and that feel is distinguished from qualities such as softness (which refers to the pliability of the fabric rather than its feel), thickness, color, or other physical characteristics not involved in smoothness of the fabric.

The panelists then assigned scores to each sample based on its order relative to the other samples; 4 having the best feel and 1 having the worst feel. The scores from each panelists were cumulated and then averaged. The results of this test are as follows:

| Amt Cellulase | Average Feel |
| --- | --- |
| None | 1.5 ± 0.5 |
| 500 ppm | 1.7 ± 0.4 |
| 1000 ppm | 3.2 ± 0.4 |
| 2000 ppm | 3.8 ± 0.4 |

The above results demonstrate that improvements in feel and appearance can be achieved with cellulase compositions free of all CBH type components.

EXAMPLE 21

Stone Washed Appearance

Example 21

This example demonstrates that the presence of CBH type components are not essential for imparting a stone washed appearance to cotton-containing fabrics. Specifically, this example employs a cellulase composition derived from *Trichoderma longibrachiatum* genetically engineered in the manner described above so as to be incapable of producing any CBH type components (i.e., incapable of producing CBH I and II components) as well as a complete cellulase composition derived from *Trichoderma longibrachiatum* and which is available as CYTOLASE 123 cellulase from Genencor International, South San Francisco, Calif.

These cellulase compositions were tested for their ability to impart a stone washed appearance to dyed cotton-containing denims pants. Specifically, the samples were prepared using an industrial washer and dryer under the following conditions:

10 mM citrate/phosphate buffer pH 5
40 L total volume
110° F.
Four pair of denim pants
1 hour run time
50 ppm CBH I and II deleted cellulase or 100 ppm whole cellulase (i.e., at approximately equal EG concentrations)

Samples were evaluated for their stonewashed appearance by 8 panelists. All eight panelists choose 100 ppm whole cellulase over non-enzyme treated pants as having the better stone washed look. Four of the 8 panelists choose the CBH I and II deleted cellulase treated pants over whole cellulase as having the better stone washed look; whereas the other panelists choose the whole cellulase treated pants as having a better stone washed look. These results indicate that the CBH I and II deleted cellulase treated pants were indistinguishable from whole cellulase treated pants and that CBH I and/or CBH II are not not essential for imparting a stone washed appearance to cotton-containing fabrics.

With regard to Examples 16 to 21, cellulase compositions free of CBH I type components and derived from microorganisms other than *Trichoderma longibrachiatum* could be used in place of the cellulase compositions described in these examples. In particular, the source of the cellulase composition containing the EG type components is not important to this invention and any fungal cellulase composition containing one or more EG type components and substantially free of all CBH I type components can be used herein. For example, fungal cellulases for use in preparing the fungal cellulase compositions used in this invention can be obtained from *Trichoderma koningii*, *Pencillum sp.*, and the like or commercially available cellulases can be used, i.e., CELLUCAST (available from Novo Industry, Copenhagen, Denmark), RAPIDASE (available from Gist Brocades, N.V., Delft, Holland), and the like.

What is claimed is:

1. In a method for enhancing the feel and/or appearance and/or for providing color enhancement and/or a stone washed appearance to cotton-containing fabrics during manufacture of the fabric by treatment of the fabric with a composition comprising a naturally complete fungal cellulase composition which comprises exo-cellobiohydrolase I component and endoglucanase component(s) wherein the improvement comprises modifying the naturally complete fungal cellulase composition to comprise at least 10 weight percent of endoglucanase components based on the total weight of protein in the fungal cellulase composition and to be free of the exo-cellobiohydrolase I component.

2. The method according to claim 1 wherein said fungal cellulase composition is also free of exo-cellobiohydrolase II component.

3. The method according to claim 1 wherein said fungal cellulase composition comprises at least about 20 weight percent of said endoglucanase component(s) based on the total weight of protein in the cellulase composition.

4. In a method for enhancing the feel and/or appearance and/or for providing color enhancement and/or a stone washed appearance to cotton-containing fabrics during manufacture of the fabric by treatment of the fabric with an aqueous fungal cellulase solution comprising a naturally complete fungal cellulase composition comprising exo-cellobiohydrolase I component and endoglucanase component(s) wherein said method is conducted with agitation under conditions so as to produce a cascading effect of the cellulase solution over the fabric wherein the improvement comprises modifying the naturally complete fungal cellulase composition to comprise at least 10 weight percent of endoglucanase component(s) based on the total weight of protein in the cellulase composition and to be free of the exo-cellobiohydrolase I component.

5. The method according to claim 4 wherein said fungal cellulase composition is also free of exo-cellobiohydrolase II component.

6. A method according to claim 4 wherein said fungal cellulase composition comprises at least about 20 weight percent of said endoglucanase component(s) based on the total weight of protein in the cellulase composition.

7. The method according to claim 1 wherein said method is conducted prior to application of a finish to said fabric.

8. The method according to claim 4 wherein said method is conducted prior to application of a finish to said fabric.

9. The method according to claim 1 wherein said composition further comprises less than about 2 weight percent of a surfactant or a mixture of surfactants.

10. The method according to claim 4 wherein said aqueous cellulase solution further comprises less than about 2 weight percent of a surfactant or a mixture of surfactants.

* * * * *

UNITED STATES PATENT AND TRADEMARK OFFICE
CERTIFICATE OF CORRECTION

PATENT NO. : 5,246,853
DATED : September 21, 1993
INVENTOR(S) : Clarkson, Larenas, Weiss Page 1 of 10

It is certified that error appears in the above-indentified patent and that said Letters Patent is hereby corrected as shown below:

On the title page, item [75]:
The second inventor's name is "Edmund Larenas", not "Edward Larenas".

UNITED STATES PATENT AND TRADEMARK OFFICE
CERTIFICATE OF CORRECTION

PATENT NO. : 5,246,853
DATED : September 21, 1993
INVENTOR(S) : Clarkson et al.

It is certified that error appears in the above-indentified patent and that said Letters Patent is hereby corrected as shown below:

in Figure 6B "*T. reesei*" should read --*T. longibrachiatum*-- and in Figure 8 both occurrences of "*T. reesei*" should read --*T. longibrachiatum*--.

at column 3, line 27, where "pΔCBHIpyr4" should read --pΔCBHI<u>pyr4</u>--; at line 29, where "cbh1" should read --<u>cbh1</u>--; at line 30, where "EcoRI" should read --<u>Eco</u>RI--, "pΔCBHIpyr4" should read --pΔCBHI<u>pyr4</u>-- and "cbh1" should read --<u>cbh1</u>--; at line 35, where "EcoRI" should read --<u>Eco</u>RI-- and "pΔCBHIpyr4" should read --pΔCBHI<u>pyr4</u>--; at line 36, where "pΔCBHIpyr4" should read --pΔCBHI<u>pyr4</u>--; at line 39, where "EcoRI" should read --<u>Eco</u>RI-- and "pΔCBHIpyr4" should read --pΔCBHI<u>pyr4</u>--; at line 49, where "cbh1" should read --<u>cbh1</u>--; at line 50, where "cbh1" should read --<u>cbh1</u>--; at line 51, where "cbh2" should read --<u>cbh2</u>--; at line 54, where --.-- should be inserted after "proteins"; at line 60, where "cbh2" should read --<u>cbh2</u>-- and "EcoRI" should read --<u>Eco</u>RI--; at line 62, where "cbh2" should read --<u>cbh2</u>--; at line 65, where "EcoRI" should read --<u>Eco</u>RI--; and at line 68, where "pEGIpyr4" should read --pEGI<u>pyr4</u>--;

UNITED STATES PATENT AND TRADEMARK OFFICE
CERTIFICATE OF CORRECTION

PATENT NO. : 5,246,853
DATED : September 21, 1993
INVENTOR(S) : Clarkson et al.

It is certified that error appears in the above-indentified patent and that said Letters Patent is hereby corrected as shown below:

at column 4, line 28, where "CDH I" should read --CBH I--;

at column 13, line 42 where "achieve" should read --achieved--;

at column 14, line 46, where "Jan. 17, 1991" should read --disclosed in U.S. Serial No. 07/642,596 filed on January 17, 1991 as Attorney Docket No. GCS-171-US1--;

at column 15, line 3, where "pyr4" should read --$pyr4^-$--; line 5 where "pyr4" should read --$pyr4$--; line 10, where "pyr4" should read --$pyr4$--; line 12, where "pyr4" should read --$pyr4$--; line 22, where "pyr4" should read --$pyr4$--; line 23, where "pyr4" should read --$pyr4$--; line 27, where "pyr4" should read --$pyr4$--; line 28, where "pyr4" should read --$pyr4$--; line 29, where "pyr4⁻" should read --$pyr4^-$--; line 32, where "CBHI" should read --CBH I--; at line 33, where "CBHI" should read --CBH I--; line 40, where "cbh1" should read --$cbh1$-- and "PstI" should read --$Pst$I--; at line 41, where "PstI" should read --$Pst$I--; at line 43, where "Kan" should read --$Kan^r$--; at line 44, where "HindIII" should

UNITED STATES PATENT AND TRADEMARK OFFICE
CERTIFICATE OF CORRECTION

PATENT NO. : 5,246,853
DATED : September 21, 1993
INVENTOR(S) : Clarkson et al.

It is certified that error appears in the above-indentified patent and that said Letters Patent is hereby corrected as shown below:

read --<u>Hin</u>dIII--; at line 47, where ""cbh1" should read --<u>cbh1</u>--; at line 49, where "PstI" should read --<u>Pst</u>I--; at line 50, where "pyr4" should read --<u>pyr4</u>--; at line 52, where "Sanbrook" should read --Sambrook--; at line 55, where "HindIII" should read --<u>Hin</u>dIII--; at line 58, where "HindIII" should read --<u>Hin</u>dIII--; at line 59, where "pyr4" should read --<u>pyr4</u>--; at line 60, where "pΔCBHIpyr4" should read --pΔCBHI<u>pyr4</u>--; and at line 68, where "pyr4⁻" should read --<u>pyr4</u>⁻--;

at column 16, line 10, where "MgSO$_4$.7H$_2$O" should read --MgSO$_4$·7H$_2$O--; at line 24, where "EcoRI" should read --<u>Eco</u>RI--; at line 25, where "pΔCBHIpyr4" should read --pΔCBHI<u>pyr4</u>--; at lines 38 and 39, where "MgSO$_4$.7H$_2$O" should read --MgSO$_4$·7H$_2$O-- and where "CaCl$_2$.2H$_2$O" should read --CaCl$_2$·2H$_2$O--; at lines 39 and 40, where "ZnSO$_4$.7H$_2$O" should read --ZnSO$_4$·7H$_2$O--; at line 40, where "Fe(NH$_4$)$_2$.6H$_2$O" should read --Fe(NH$_4$)$_2$·6H$_2$O-- and "CuSO$_4$.5H$_2$O" should read --CuSO$_4$·5H$_2$O--; and at line 41, where "MnSO$_4$.4H$_2$O" should read --MnSO$_4$·4H$_2$O--; at line 47, where "pyr4" should read

UNITED STATES PATENT AND TRADEMARK OFFICE
CERTIFICATE OF CORRECTION

PATENT NO. : 5,246,853
DATED : September 21, 1993
INVENTOR(S) : Clarkson et al.

It is certified that error appears in the above-indentified patent and that said Letters Patent is hereby corrected as shown below:

--pyr4--; at line 48, where "pyr4" should read --pyr4--; at line 49, where "pΔCBHIpyr4" should read --pΔCBHIpyr4--; at line 59, where "PstI" should read --PstI--; at line 63, where "pΔCBHIpyr4" should read --pΔCBHIpyr4--; at line 64, where "cbh1" should read --cbh1-- and "PstI" should read --PstI--; at line 65, where "pyr4" should read --pyr4--; at line 67, where "cbh1" should read --cbh1--; and at line 68, where "EcoRI" should read --EcoRI--;

at column 17, line 1, where "pΔCBHIpyr4" should read
--pΔCBHIpyr4-- and "cbh1" should read --cbh1--; at line 2, where --chromosomes-- should be inserted after "longibrachiatum"; at line 14, where "cbh1" should read --cbh1--; at line 18, where "pΔCBHIpyr4" should read --pΔCBHIpyr4--; at line 19, where "pyr4" should read --pyr4--; at line 25, where "BglII" should read --BglII--; at line 26, where "cbh1" should read --cbh1--; at line 31, where "cbh1" should read --cbh1--; at line 33, where "cbh1" should read --cbh1--; at line 39, where "Trichoderma" should read --Trichoderma--; at line 42, where "CuSO4.5H2O" should read --$CuSO_4 \cdot 5H_2O$--; at line 43, where "FeSO4.7H2O" should read --$FeSO_4 \cdot 7H_2O$-- and "ZnSO4.7H2O" should read

UNITED STATES PATENT AND TRADEMARK OFFICE
CERTIFICATE OF CORRECTION

PATENT NO. : 5,246,853  
DATED : September 21, 1993  
INVENTOR(S) : Clarkson et al.

It is certified that error appears in the above-indentified patent and that said Letters Patent is hereby corrected as shown below:

--$ZnSO_4 \cdot 7H_2O$--; at line 44, where "$Na_2MoO_4.2H_2O$" should read --$Na_2MoO_4 \cdot 2H_2O$--; at line 45, where "$MnCl.4H_2O$" should read --$MnCl \cdot 4H_2O$--; at line 59, where "cbh1" should read --<u>cbh1</u>--; and at line 67, where "cbh1" should read --<u>cbh1</u>--;

at column 18, line 1, where "CBHI" should read --CBH I--; at line 5, where "CBHI" should read --CBH I-- and "cbh1" should read --<u>cbh1</u>--; at line 10, where "cbh2" should read --<u>cbh2</u>--; at line 12, where "EcoRI" should read --<u>Eco</u>RI--; at line 17, where "HindIII" should read --<u>Hin</u>dIII--; at line 18, where "ClaI" should read --<u>Cla</u>I--; at line 20, where "pyr4" should read --<u>pyr4</u>--; at line 21, where "EcoRI" should read --<u>Eco</u>RI--; at line 22, where "cbh2" should read --<u>cbh2</u>--; at line 23, where "cbh2" should read --<u>cbh2</u>--; at line 25, where "pyr4" should read --<u>pyr4</u>--; at line 28, where "pyr4-" should read --<u>pyr4</u>$^-$--; at line 30, where "cbh1" should read --<u>cbh1</u>--; at line 31, where "pyr4$^-$" should read --<u>pyr4</u>$^-$--; at line 33, where "pyr4$^-$" should read --<u>pyr4</u>$^-$--; at line 38, where "cbh2" should read --<u>cbh2</u>--; and at line 39, where "cbh1" should read --<u>cbh1</u>--; at line 41, where "EcoRI" should read --<u>Eco</u>RI--; at line 50, where "cbh1 and cbh2"

UNITED STATES PATENT AND TRADEMARK OFFICE
CERTIFICATE OF CORRECTION

PATENT NO. : 5,246,853
DATED : September 21, 1993
INVENTOR(S) : Clarkson et al.

It is certified that error appears in the above-indentified patent and that said Letters Patent is hereby corrected as shown below:

should read --<u>cbh1</u> and <u>cbh2</u>--; at line 53, where "EcoRI and Asp718" should read --<u>Eco</u>RI and <u>Asp</u>718--; at line 59, where "EcoRI" should read --<u>Eco</u>RI--; at line 60, where "cbh2" should read --<u>cbh2</u>--; at line 64, where "EcoRI" should read --<u>Eco</u>RI--; at line 66, where "cbh2" should read --<u>cbh2</u>--; and at line 68, where "EcoRI" should read --<u>Eco</u>RI--.

at column 19, line 2, where "cbh2" should read --<u>cbh2</u>--; at line 3, where "cbh2" should read --<u>cbh2</u>--; at line 6, where "cbh2" should read --<u>cbh2</u>--; at line 12, where "egl1" should read --<u>egl1</u>--; at line 13, where "HindIII" should read --<u>Hin</u>dIII--; at line 17, where "HindIII-BamHI" should read --<u>Hin</u>dIII-<u>Bam</u>HI--; at lines 18 and 19, where "HindIII-BamHI" should read --<u>Hin</u>dIII-<u>Bam</u>HI--; at line 20, where "pyr4" should read --<u>pyr4</u>--; at line 21, where "HindIII" should read --<u>Hin</u>dIII-- and "pEGIpyr4" should read --pEGI<u>pyr4</u>--; at line 22, where "pEGIpyr4" should read --pEGI<u>pyr4</u>-- and "HindIII" should read --<u>Hin</u>dIII--; at line 24, where "egl1" should read --<u>egl1</u>-- and "pyr4" should read --<u>pyr4</u>--; at

UNITED STATES PATENT AND TRADEMARK OFFICE
CERTIFICATE OF CORRECTION

PATENT NO. : 5,246,853
DATED : September 21, 1993
INVENTOR(S) : Clarkson et al.

It is certified that error appears in the above-indentified patent and that said Letters Patent is hereby corrected as shown below:

line 31, where "pEGIpyr4" should read --pEGI<u>pyr4</u>"; at line 32, where "pyr4" should read --<u>pyr4</u>--; and at line 37, where "pyr4" should read --<u>pyr4</u>--; at line 47 where "MgSO$_4$.7H$_2$O" should read --MgSO$_4$·7H$_2$O-- and "FeSO$_4$.7H$_2$O" should read --FeSO$_4$·7H$_2$O--; and at line 48 where "MnSO$_4$.H$_2$O" should read --MnSO$_4$·H$_2$O--;

at column 20, line 6, where "xg" should read --x g--; at line 34, where "pEGIpyr4" should read --pEGI<u>pyr4</u>--; at line 37, where "pEGIpyr4" should read --pEGI<u>pyr4</u>--; at line 45, where "pEGIpyr4" should read --pEGI<u>pyr4</u>--; at line 46, where "cbh1" should read --<u>cbh1</u>-- and "cbh2" should read --<u>cbh2</u>--; at line 53, where "(<u>Trichoderma longibrachiatum</u>)" should read --<u>Trichoderma longibrachiatum</u> (<u>T. longibrachiatum</u>)--; at line 55, where "TABLE 1" should read --TABLE 1
Secreted endoglucanase activity of
<u>T. longibrachiatum</u> transformants--

UNITED STATES PATENT AND TRADEMARK OFFICE
CERTIFICATE OF CORRECTION

PATENT NO. : 5,246,853
DATED : September 21, 1993
INVENTOR(S) : Clarkson et al.

It is certified that error appears in the above-indentified patent and that said Letters Patent is hereby corrected as shown below:

at column 22, line 13, where "0%" should read --10%--; and at line 22, where "Calif.:" should read --Calif.)--;

at column 25, at lines 33 and 34, where both occurrences of "_FTS_" should read --FTS--; and at line 68, where "example" should read --examples--;

at column 29, line 11, where "solution" should read --solutions--;

at column 30, line 27, where "were assigned" should be deleted; and

UNITED STATES PATENT AND TRADEMARK OFFICE
CERTIFICATE OF CORRECTION

PATENT NO. : 5,246,853
DATED : September 21, 1993
INVENTOR(S) : Clarkson et al.

It is certified that error appears in the above-indentified patent and that said Letters Patent is hereby corrected as shown below:

at column 31, line 23, where "Example 21" should be deleted; at line 37, where "denims" should read --denim--. and at line 58, where the second occurrence of "not" should be deleted.

Signed and Sealed this

Twentieth Day of June, 1995

Attest:

BRUCE LEHMAN

Attesting Officer

Commissioner of Patents and Trademarks